US010202546B2

(12) United States Patent
Han et al.

(10) Patent No.: US 10,202,546 B2
(45) Date of Patent: Feb. 12, 2019

(54) LIGANDS FOR SEMICONDUCTOR NANOCRYSTALS

(71) Applicant: Massachusetts Institute of Technology, Cambridge, MA (US)

(72) Inventors: Hee-Sun Han, Cambridge, MA (US); Wenhao Liu, Cambridge, MA (US); Moungi G. Bawendi, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/701,425

(22) Filed: Sep. 11, 2017

(65) Prior Publication Data

US 2018/0187072 A1 Jul. 5, 2018

Related U.S. Application Data

(63) Continuation-in-part of application No. 13/069,458, filed on Mar. 23, 2011, now Pat. No. 9,759,727.

(60) Provisional application No. 61/316,659, filed on Mar. 23, 2010.

(51) Int. Cl.
| | |
|---|---|
| *C09K 11/02* | (2006.01) |
| *A61K 49/00* | (2006.01) |
| *C09K 11/88* | (2006.01) |
| *C08F 220/60* | (2006.01) |
| *C08F 230/00* | (2006.01) |
| *G01N 21/64* | (2006.01) |
| *C09K 11/56* | (2006.01) |

(52) U.S. Cl.
CPC ........ *C09K 11/025* (2013.01); *A61K 49/0041* (2013.01); *A61K 49/0054* (2013.01); *A61K 49/0093* (2013.01); *C08F 220/60* (2013.01); *C08F 230/00* (2013.01); *C09K 11/565* (2013.01); *C09K 11/883* (2013.01); *G01N 21/6428* (2013.01); *G01N 2021/6439* (2013.01)

(58) Field of Classification Search
CPC ... C09K 11/025; C09K 11/565; C09K 11/883; A61K 49/0041; A61K 49/0093; A61K 49/0054; G01N 21/6428; G01N 2021/6439; C08F 230/00; C08F 220/60
See application file for complete search history.

(56) References Cited

U.S. PATENT DOCUMENTS

| | | | |
|---|---|---|---|
| 6,322,901 | B1 | 11/2001 | Bawendi et al. |
| 6,576,291 | B2 | 6/2003 | Bawendi et al. |
| 7,198,847 | B2 | 4/2007 | Naasani |
| 7,205,048 | B2 | 4/2007 | Naasani |
| 7,390,568 | B2 | 6/2008 | Kim et al. |
| 2005/0112376 | A1 | 5/2005 | Naasani |

FOREIGN PATENT DOCUMENTS

| | | |
|---|---|---|
| WO | 2006033732 | 3/2006 |
| WO | 2007018647 | 2/2007 |
| WO | 2009146157 | 12/2009 |

OTHER PUBLICATIONS

Liu, W. et al. J. Am. Chem. Soc. 2010, 132(2), 472-483.
Muro et al., J. Am. Chem. Soc. 2010, 132(13): 4556-4557.
Medintz et al., Nat. Mater., 2005, 4(6): 435-446.
Shen et al., J.Mater. Chem, 2008, 18, 763-770.
Aaron R. Clapp, et al. ChemPhysChem 2006, 7, (I), 47-57.
Ballou, B. et al. Bioconjug. Chern. 2004, 15,79-86.
Bentzen, E. L. et al. Bioconjugate Chemistry 2005, 16, (6), 1488-1494.
Brown, E. B. et al. Nat Med 2001, 7, 864-868.
Chen, S. et al. 1. Am. Chem. Soc. 2005,127, 14473-14478.
Chiefari, J. et al. Macromolecules 1998,31, (16),5559-5562.
Choi, H. S. et al. Nat. Biotech. 2007,25, 1165-70.
Duda, D. G. et al. 2004; vol. 64, p. 5920-5924.
Groc, L. et al. Nat. Neurosci. 2004, 7, 695-696.
Holmlin, R. E. et al. Langmuir 2001, 17, 2841-2850.
Howarth, M. et al. Nat Meth 2008, 5, (5), 397-399.
Howarth, M. et al. Proc Natl Acad Sci USA. 2005,102,7583-7588.
Huang, P.; et al. J. Am Chem. Soc. 2008, 47, 170-170.
Jain, R. K et al. Nat Rev Cancer 2002, 2, 266-276.
Jia, G. et al. Langmuir 2009,25, 3196-3199.
Jin Q. et al. Chem. Commun. 2008, 3058-3060.
Ladd, J. et al. Biomncromolecules 2008,9, 1357-1361.
Leatherdale, C. A. et al. J. Phys. Chem. B. 2002, 106, 7619-7622.
Liu, W. et al. J. Am. Chem. Soc. 2007,129, 14530-14531.
Liu, W. et al. J. Am. Chem. Soc. 2008, 130, 1274-1284.
Medintz, I. L. et al. Bioconjugate Chemistry 2008, 19, (9), 1785-1795.
Peng, Z. A.; Peng, X. J. Am. Chem. Soc. 2001, 123, 183-184.

(Continued)

*Primary Examiner* — Robert S Cabral
(74) *Attorney, Agent, or Firm* — Steptoe & Johnson LLP

(57) ABSTRACT

In this invention, polyimidazole ligands (PILs) incorporating pendant imidazole moieties for nanocrystal binding and either sulfonatebetaine, carboxybetaine, or phosphocholinebetaine moieties for water-solubilization have been developed. Greatly enhanced stability of nanocrystals (both over time and in wide pH range) was achieved by incorporating multi-dentate imidazole moieties which provide strong coordination of the ligand to the nanocrystal surface and prevent aggregation of nanocrystals. Synthesis of betaine PILs was developed by modifying the synthesis of recently developed PEG containing poly imidazole ligands (PEG PILs). These nanocrystals are compact, water soluble, and biocompatible.

10 Claims, 9 Drawing Sheets

(56) References Cited

OTHER PUBLICATIONS

Sapsford, K. E. et al. J. Phys. Chem. C. 2007, III, (11528-11538).
Snee, P. T. et al. Adv. Mater. 2005, 17, 1131-1136.
Yildiz, I. et al. Langmuir 2009, 25, (12), 7090-7096.

US 10,202,546 B2

LIGANDS FOR SEMICONDUCTOR NANOCRYSTALS

CLAIM OF PRIORITY

This application is a continuation of U.S. application Ser. No. 13/069,458, filed Mar. 23, 2011, which claims priority to U.S. Provisional Application No. 61/316,659, filed Mar. 23, 2010, each of which is incorporated by reference in its entirety.

FEDERALLY SPONSORED RESEARCH

This invention was made with government support under Grant Numbers 5R01CA126642-02 and 5-U54-CA1193949-05, awarded by the National Institutes of Health. The government has certain rights in the invention.

FIELD OF THE INVENTION

This invention relates to ligands for semiconductor nanocrystals.

BACKGROUND

Poly(ethylene glycol) (PEG) has been one of the most popular surface coatings for nanoparticles to make them water soluble and not interacting with biomolecules or cells. See, for example, Bentzen, E. L. et al. *Bioconjug. Chem.* 2005, 16, 1488-1494; and Ballou, B. et al. *Bioconjug. Chem.* 2004, 15, 79-86, each of which is incorporated by reference in its entirety. However, PEG coatings can add significant hydrodynamic diameter to the nanoparticles, for example when more than 8 units of ethylene glycol are required for water solubilization of the particles. For instance, PEG coatings produce hydrodynamic diameter of greater than 10 nm for an inorganic core/shell of <5 nm. See, for example, Liu, W. et al. *J. Am. Chem. Soc.* 2008, 130, 1274-1284; and Liu, W. et al. *J. Am. Chem. Soc.* 2010, 132, 472-483, each of which is incorporated by reference in its entirety. Small hydrodynamic diameter can favor desirable properties, such as to crowded regions for biological studies, efficient Förster Resonance Energy Transfer (FRET), and renal clearance of the particles. See, for example, Howarth, M. et al. *Proc Natl Acad Sci USA*. 2005, 102, 7583-7588; Groc, L. et al. *Nat. Neurosci.* 2004, 7, 695-696; Choi, H. S. et al. *Nat. Biotech.* 2007, 25, 1165-70, each of which is incorporated by reference in its entirety. Identifying more compact ligands has been an issue in the field.

SUMMARY

Semiconductor nanocrystals have size-dependent optical and electronic properties. In particular, the band gap energy of a semiconductor nanocrystal of a particular semiconductor material varies with the diameter of the crystal.

Monodisperse particles can be defined as having at least 60% of the particles fall within a specified particle size range. Monodispersed particles deviate less than 10% in rms diameter and preferably less than 5%.

In one embodiment, a water soluble composition can include a plurality of semiconductor nanocrystals and a polyimidazole ligand including a zwitterionic moiety coat on each semiconductor nanocrystal of the plurality of semiconductor nanocrystals. The zwitterionic moiety can include betaine. In one embodiment, the betaine polyimidazole ligand coat can include a sulfonate. In another embodiment, the betaine polyimidazole ligand coat can include a carboxylate. In another embodiment, the betaine polyimidazole ligand coat can include a phosphocholine.

In one embodiment, the plurality of semiconductor nanocrystals can be substantially monodisperse. In one embodiment, the hydrodynamic diameter can be no larger than 10 nm. In another embodiment, the hydrodynamic diameter can be no larger than 7 nm.

In one embodiment, the composition can be biocompatible. In another embodiment, the composition can include an energy transfer dye. The composition can exhibit high permeability in blood vessels. The blood vessels can be tumor vessels. In one embodiment, the composition can exhibit low non-specific binding to cells and macromolecules. The macromolecules can be proteins. The proteins can be on the surface of the cell or within the cell. In another embodiment, the quantum yield of the composition can be greater than 50%.

In one embodiment, a method of making a water-soluble semiconductor nanocrystal can include purifying imidazole monomers, purifying tertiary amine monomers; polymerizing imidazole and tertiary amine monomers, and exchanging the ligand of a capped semiconductor nanocrystal with the imidazole polymer including a zwitterionic moiety. The method can include betainisation of the imidazole polymer before deprotecting a BOC group. The method can further include deprotecting the BOC group on the imidazole polymer before exchanging the ligand of a capped semiconductor nanocrystal. In one embodiment, the method can result in a sulfonate betaine polymer. In another embodiment, the betainisation of the imidazole polymer can result in a carboxylate betaine polymer. In another embodiment, the betainisation of the imidazole polymer can result in a phosphocholine betaine polymer.

In one embodiment a method of biological in vivo imaging can include introducing betaine polyimidazole ligand including a zwitterionic moiety coated semiconductor nanocrystals to the subject, allowing the semiconductor nanocrystals to diffuse, and visualizing the image with photon laser scanning microscopy. Visualizing the image can be with one-photon or two-photon laser scanning microscopy. In another embodiment, the semiconductor nanocrystals can be used to image the extravasation of the nanocrystals from microvessels into a tumor.

In one embodiment a method of biological in vitro imaging including introducing betaine polyimidazole ligand including a zwitterionic moiety coated semiconductor nanocrystals to a biological sample, allowing the semiconductor nanocrystals to diffuse, collecting data from the semiconductor nanocrystals, and visualizing an image from the data.

Other embodiments are within the scope of the claims.

DETAILED DESCRIPTION

Figure 1:
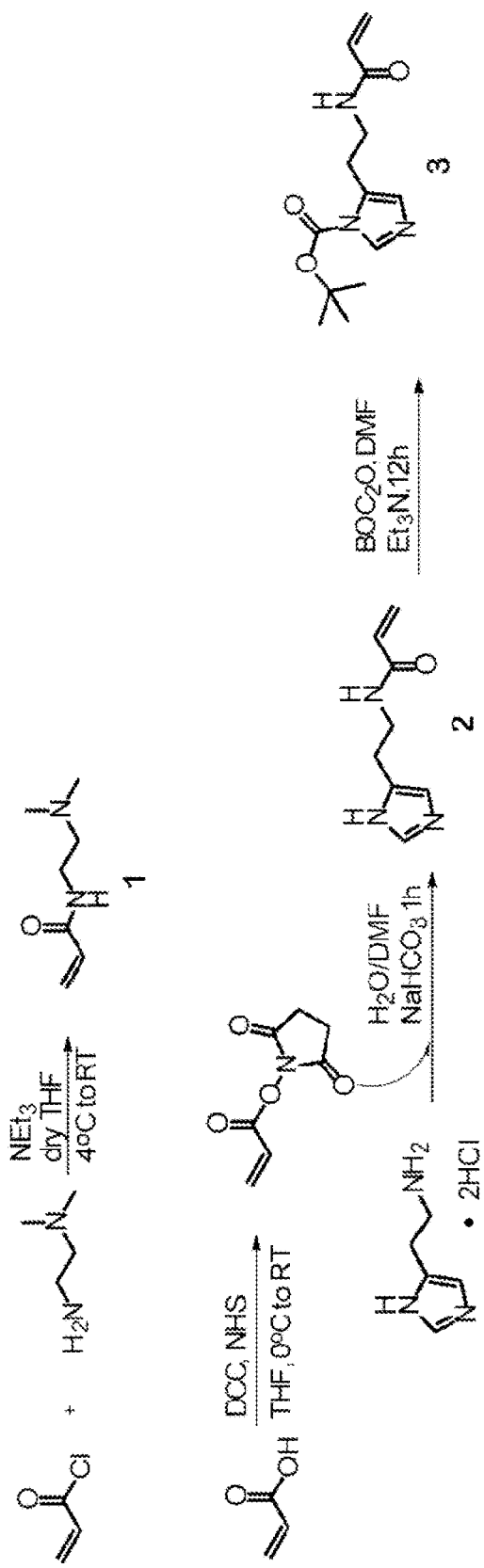
FIG. 1 is a schematic of the synthesis of compound 1 (top) and compound 3 (bottom).

Zwitterionic self assembled monolayers (SAMs) can assist in forming a biocompatible surface. Due to the strong hydration capacity via electrostatic interactions, zwitterionic SAMs can show very low non-specific protein adsorption. See, for example, Holmlin, R. E. et al. *Langmuir* 2001, 17, 2841-2850; Chen, S. et al. *J. Am. Chem. Soc.* 2005, 127, 14473-14478; Ladd, J. et al. *Biomacromolecules* 2008, 9, 1357-1361, each of which is incorporated by reference in its entirety. Small molecules containing zwitterionic moieties, such as cysteine or mercaptoalkane-phosphorylcholine, have been used to prepare water soluble nanocrystals or gold nanoparticles. See, for example, Liu, W. et al. *J. Am. Chem. Soc.* 2007, 129, 14530-14531; and Jin Q. et al. *Chem. Commun.* 2008, 3058-3060, each of which is incorporated in its entirety. A zwitterionic moiety is a part of structure that has positive and negative charges and can have a total net charge of zero.

A semiconductor nanocrystal can be bound to or otherwise associated with zwitterionic polyimidazole ligands (zwitterionic PILs) incorporating pendant imidazole moieties for nanocrystal binding and zwitterionic structures (for example, either sulfonatebetaine or carboxybetaine moieties) for water-solubilization. Greatly enhanced stability of nanocrystals (both over time and in wide pH range) was achieved by incorporating multi-dentate imidazole moieties which provide strong coordination of the ligand to the nanocrystal surface and prevent aggregation of nanocrystals.

Zwitterionic PIL synthesis can be accomplished by either random or block copolymerization. The zwitterionic PIL can have the following general formula:

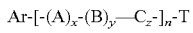

wherein

Ar is an optionally substituted aryl group or an optionally substituted heteroaryl group;

A is a monomeric unit including a pendant zwitterion;

B is a monomeric unit including a moiety having an affinity for a surface of a nanocrystal;

C is a monomeric unit including a selectively reactive functional moiety;

T is a terminating moiety;

each of x, y, z, and n, independently, is an integer, for example, 1-100, 1-50, 1-25, 2, 3, 4, 5, 6, 7, 8, 9, 10, 11, 12, 13, 14, 15, 16, 17, 18, 19, and 20.

In some embodiments, Ar is phenyl or substituted phenyl. Monomeric units A and B can be derived from monomers suitable for radical polymerization. Monomer units A and B can be derived from olefinically unsaturated monomers, such as, e.g., alpha-olefins, acrylates, acrylamides, vinyl monomers, styryl monomers, methacrylate, methacrylamides, and the like. Monomeric units A and B can be chemically modified relative to the monomer form; in other words, monomers can be polymerized, and the resulting polymer further modified, e.g., to add a zwitterionic moiety to some monomer units; or in another example, to deprotect a functional group that was protected during polymerization.

In some embodiments, -A- can have the formula

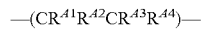

where each of $R^{A1}$, $R^{A2}$, $R^{A3}$, and $R^{A4}$, independently, can be H, halo, hydroxy, alkyl, alkenyl, alkynyl, cycloalkyl, alkoxy, aryl, heteroaryl, or heterocyclyl, or can have the formula:

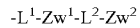

where $L^1$ is —O—, —CO—, —NR$^a$—, —S—, —(CR$^a$R$^b$)$_m$—, or a combination thereof; $Zw^1$ is a first ionized or ionizable moiety, $L^2$ is —O—, —CO—, —NR$^a$—, —S—, —(CR$^a$R$^b$)$_m$—, or a combination thereof; and $Zw^2$ is a second ionized or ionizable moiety.

In some embodiments, $Zw^1$ is selected from —(NR$^a$R$^b$)$^+$— and —(OP(O)$_2$O)$^-$—, and $Zw^2$ is selected from —(NR$^a$R$^b$R$^c$)+, —(SO$_3$)$^-$, and —(PO$_4$)$^-$. $L^1$ can be —C(O)NH—. $L^2$ can be —(CR$^a$R$^b$)$_m$—.

Each $R^a$, $R^b$, and $R^c$, independently, is H, alkyl, alkenyl, alkynyl, cycloalkyl, alkoxy, aryl, heteroaryl, or heterocyclyl. In some cases, each $R^a$, $R^b$, and $R^c$, independently, can be H or alkyl.

Each m, independently, is an integer from 1 to 6.

In some cases, $R^{A2}$, $R^{A3}$, and $R^{A4}$, can each independently be H or alkyl. $R^{A2}$ and $R^{A3}$ can be H and $R^{A4}$ can be H or methyl.

In some embodiments, —B— can have the formula

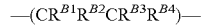

where each of $R^{B1}$, $R^{B2}$, $R^{B3}$, and $R^{B4}$, independently, can be H, halo, hydroxy, alkyl, alkenyl, alkynyl, cycloalkyl, alkoxy, aryl, heteroaryl, or heterocyclyl, or can have the formula:

where $L^3$ is —O—, —CO—, —NR$^a$—, —S—, —(CR$^a$R$^b$)$_m$—, or a combination thereof; $L^4$ is —O—, —CO—, —NR$^a$—, —S—, —(CR$^a$R$^b$)$_m$—, or a combination thereof; and Het is —OR$^5$, —SR$^{B5}$, —NR$^a$R$^{B5}$, PR$^a$R$^b$, P(O)R$^a$R$^b$, or a 3 to 8 membered heteroaryl group including 1 to 3 ring atoms selected from O, N and S, or a 3 to 8 membered heterocyclyl group including 1 to 3 ring atoms selected from O, N and S.

$R^{B5}$ is H, alkyl, alkenyl, alkynyl, cycloalkyl, alkoxy, aryl, heteroaryl, or heterocyclyl.

In some embodiments, Het can be 5 to 7 membered heteroaryl group or a 5 to 7 membered heterocyclyl group where 1-3 ring atoms are N. Het can include an —NH— moiety.

Het can be an imidazolyl group, e.g., 1H-imidazol-4-yl.

In some embodiments, C can have the formula:

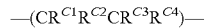

where each of $R^{C1}$, $R^{C2}$, $R^{C3}$, and $R^{C4}$, independently, can be H, halo, hydroxy, alkyl, alkenyl, alkynyl, cycloalkyl, alkoxy, aryl, heteroaryl, or heterocyclyl, or can have the formula:

$$-L^1-R^{C5}$$

where $L^1$ is —O—, —CO—, —NR$^a$—, —S—, —(CR$^a$R$^b$)$_m$—, or a combination thereof; and $R^{C5}$ is a reactive functional moiety. The reactive moiety can include a protecting group, nucleophilic group or electrophilic group. In some cases, $R^{C5}$ is selected from halo, formyl, —OH, —SH, and —NHR$^a$.

T can be —OR$^a$, —SR$^a$, —NR$^a$R$^b$, halo, alkyl, alkenyl, alkynyl, cycloalkyl, alkoxy, aryl, heteroaryl, or heterocyclyl. In some cases, T is —SH.

Examples of the zwitterionic PIL include the following:

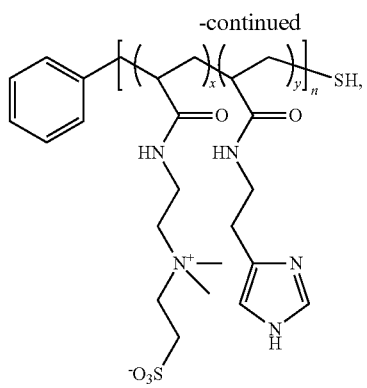

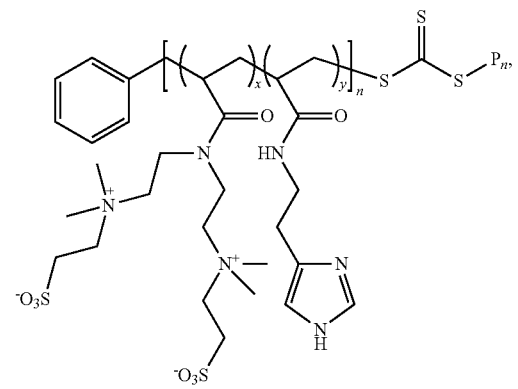

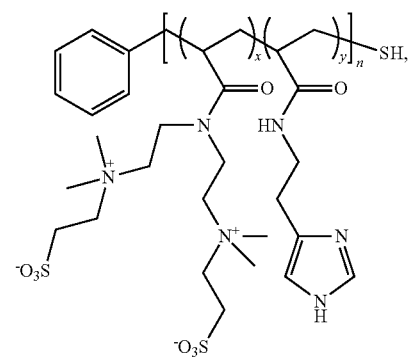

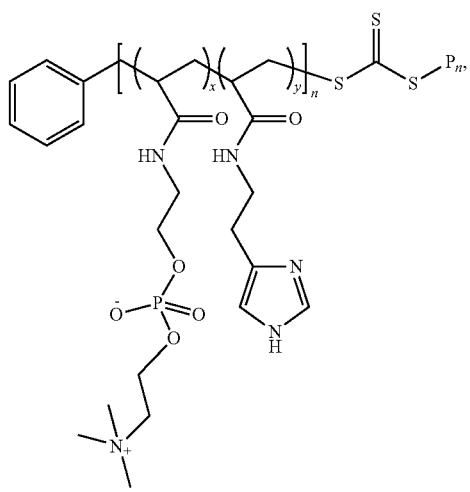

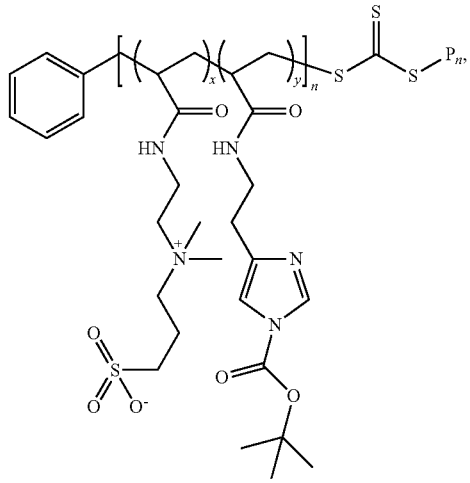

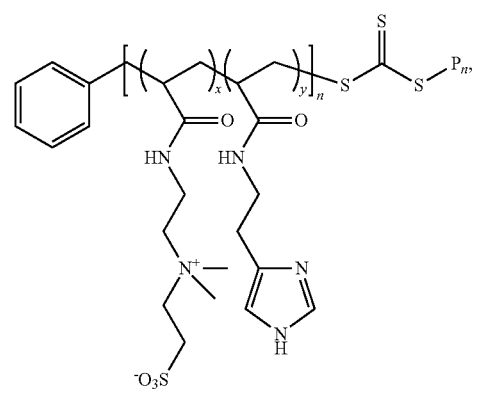

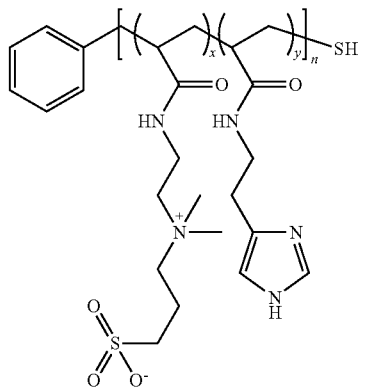

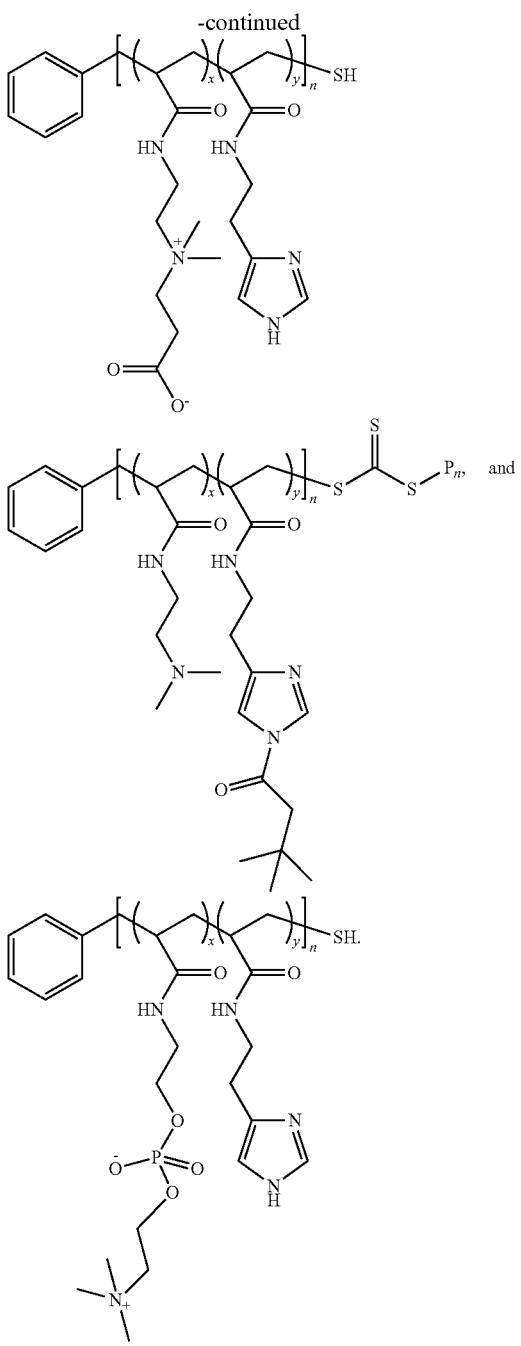

Polymers can be synthesized with acrylate monomers instead of acrylamide monomers as described above. Also the terminating group can be varied depending on the choice of RAFT agent.

An example of a zwitterionic PIL is a betaine PIL. Synthesis of betaine PILs was developed by modifying the synthesis of recently developed PEG containing poly imidazole ligands (PEG PILs). See, for example, Liu, W. et al. J. Am. Chem. Soc. 2010, 132, 472-483, which is incorporated by reference in its entirety.

Semiconductor nanocrystals demonstrate quantum confinement effects in their luminescent properties. When semiconductor nanocrystals are illuminated with a primary energy source, a secondary emission of energy occurs at a frequency that relates to the band gap of the semiconductor material used in the nanocrystal. In quantum confined particles, the frequency is also related to the size of the nanocrystal.

In general, the method of manufacturing a nanocrystal is a colloidal growth process. See, for example, U.S. Pat. Nos. 6,322,901 and 6,576,291, each of which is incorporated by reference in its entirety. Colloidal growth occurs by rapidly injecting an M-containing compound and an X donor into a hot coordinating solvent. The coordinating solvent can include an amine. The M-containing compound can be a metal, an M-containing salt, or an M-containing organometallic compound. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating solvent that follows nucleation can also result in uniform surface derivatization and regular core structures. As the size distribution sharpens, the temperature can be raised to maintain steady growth. By adding more M-containing compound or X donor, the growth period can be shortened. The betaine PIL polymer can also be used with polydisperse semiconductor nanocrystals.

The M-containing salt can be a non-organometallic compound, e.g., a compound free of metal-carbon bonds. M can be cadmium, zinc, magnesium, mercury, aluminum, gallium, indium, thallium, or lead. The M-containing salt can be a metal halide, metal carboxylate, metal carbonate, metal hydroxide, metal oxide, or metal diketonate, such as a metal acetylacetonate. The M-containing salt is less expensive and safer to use than organometallic compounds, such as metal alkyls. For example, the M-containing salts are stable in air, whereas metal alkyls are generally unstable in air. M-containing salts such as 2,4-pentanedionate (i.e., acetylacetonate (acac)), halide, carboxylate, hydroxide, oxide, or carbonate salts are stable in air and allow nanocrystals to be manufactured under less rigorous conditions than corresponding metal alkyls.

Suitable M-containing salts include cadmium acetylacetonate, cadmium iodide, cadmium bromide, cadmium chloride, cadmium hydroxide, cadmium carbonate, cadmium acetate, cadmium oxide, zinc acetylacetonate, zinc iodide, zinc bromide, zinc chloride, zinc hydroxide, zinc carbonate, zinc acetate, zinc oxide, magnesium acetylacetonate, magnesium iodide, magnesium bromide, magnesium chloride, magnesium hydroxide, magnesium carbonate, magnesium acetate, magnesium oxide, mercury acetylacetonate, mercury iodide, mercury bromide, mercury chloride, mercury hydroxide, mercury carbonate, mercury acetate, aluminum acetylacetonate, aluminum iodide, aluminum bromide, aluminum chloride, aluminum hydroxide, aluminum carbonate, aluminum acetate, gallium acetylacetonate, gallium iodide, gallium bromide, gallium chloride, gallium hydroxide, gallium carbonate, gallium acetate, indium acetylacetonate, indium iodide, indium bromide, indium chloride, indium hydroxide, indium carbonate, indium acetate, thallium acetylacetonate, thallium iodide, thallium bromide, thallium chloride, thallium hydroxide, thallium carbonate, or thallium acetate.

Alkyl is a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Optionally, an alkyl can contain 1 to 6 linkages selected from the group consisting of —O—, —S—, -M- and —NR— where R is hydrogen, or $C_1$-$C_8$ alkyl or lower alkenyl.

Prior to combining the M-containing salt with the X donor, the M-containing salt can be contacted with a coordinating solvent to form an M-containing precursor. Typical coordinating solvents include alkyl phosphines, alkyl phosphine oxides, alkyl phosphonic acids, or alkyl phosphinic acids; however, other coordinating solvents, such as pyridines, furans, and amines may also be suitable for the nanocrystal production. Examples of suitable coordinating solvents include pyridine, tri-n-octyl phosphine (TOP) and tri-n-octyl phosphine oxide (TOPO). Technical grade TOPO can be used. The coordinating solvent can include a 1,2-diol or an aldehyde. The 1,2-diol or aldehyde can facilitate reaction between the M-containing salt and the X donor and improve the growth process and the quality of the nanocrystal obtained in the process. The 1,2-diol or aldehyde can be a $C_6$-$C_{20}$ 1,2-diol or a $C_6$-$C_{20}$ aldehyde. A suitable 1,2-diol is 1,2-hexadecanediol or myristol and a suitable aldehyde is dodecanal is myristic aldehyde.

The X donor is a compound capable of reacting with the M-containing salt to form a material with the general formula MX. Typically, the X donor is a chalcogenide donor or a pnictide donor, such as a phosphine chalcogenide, a bis(silyl) chalcogenide, dioxygen, an ammonium salt, or a tris(silyl) pnictide. Suitable X donors include dioxygen, elemental sulfur, bis(trimethylsilyl) selenide ($(TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl)telluride ($(TMS)_2Te$), sulfur, bis(trimethylsilyl)sulfide ($(TMS)_2S$), a trialkyl phosphine sulfide such as (tri-n-octylphosphine) sulfide (TOPS), tris(dimethylamino) arsine, an ammonium salt such as an ammonium halide (e.g., $NH_4Cl$), tris(trimethylsilyl) phosphide ($(TMS)_3P$), tris(trimethylsilyl) arsenide ($(TMS)_3As$), or tris(trimethylsilyl) antimonide ($(TMS)_3Sb$). In certain embodiments, the M donor and the X donor can be moieties within the same molecule.

The nanocrystal manufactured from an M-containing salt grows in a controlled manner when the coordinating solvent includes an amine. The amine in the coordinating solvent can contribute to the quality of the nanocrystal obtained from the M-containing salt and X donor. Preferably, the coordinating solvent is a mixture of the amine and an alkyl phosphine oxide in a mole ratio of 10:90, more preferably 30:70 and most preferably 50:50. The combined solvent can decrease size dispersion and can improve photoluminescence quantum yield of the nanocrystal. The preferred amine is a primary alkyl amine or a primary alkenyl amine, such as a $C_2$-$C_{20}$ alkyl amine, a $C_2$-$C_{20}$ alkenyl amine, preferably a $C_8$-$C_{18}$ alkyl amine or a $C_8$-$C_{18}$ alkenyl amine. For example, suitable amines for combining with tri-octylphosphine oxide (TOPO) include 1-hexadecylamine, or oleylamine. When the 1,2-diol or aldehyde and the amine are used in combination with the M-containing salt to form a population of nanocrystals, the photoluminescence quantum efficiency and the distribution of nanocrystal sizes are improved in comparison to nanocrystals manufactured without the 1,2-diol or aldehyde or the amine.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, both CdSe and CdS can be tuned in the visible region and InAs can be tuned in the infrared region.

A population of nanocrystals can have a narrow size distribution. The population can be monodisperse and can exhibit less than a 15% rms deviation in diameter of the nanocrystals, preferably less than 10%, more preferably less than 5%. Spectral emissions in a narrow range of between 10 and 100 nm full width at half max (FWHM) can be observed. Semiconductor nanocrystals can have emission quantum efficiencies of greater than 2%, 5%, 10%, 20%, 40%, 60%, 70%, or 80%.

The semiconductor forming the core of the nanocrystal can include Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

The quantum efficiency of emission from nanocrystals having a core of a first semiconductor material can be enhanced by applying an overcoating of a second semiconductor material such that the conduction band of the second semiconductor material is of higher energy than that of the first semiconductor material, and the valence band of the second semiconductor material is of lower energy than that of the first semiconductor material. As a result, charge carriers, i.e., electrons and holes, are confined in the core of the nanocrystal when in an excited state. Alternatively, the conduction band or valence band of overcoating material can have an energy intermediate between the energies of the conduction and valence bands of the core material. In this case, one carrier can be confined to the core while the other is confined to the overcoating material when in an excited state. See, for example, U.S. patent application Ser. No. 10/638,546, which is incorporated by reference in its entirety. The core can have an overcoating on a surface of the core. The band gap of core and overcoating can have a desired band offset. In CdTe/CdSe (core/shell) nanocrystals, the conduction band of the shell is intermediate in energy to the valence band and conduction band of the core. CdTe/CdSe (core/shell) nanocrystals have lower potentials for the holes in the core and for the electrons in the shell. As a result, the holes can be mostly confined to the CdTe core, while the electrons can be mostly confined to the CdSe shell. CdSe/ZnTe (core/shell) nanocrystals have the valence band of the shell intermediate in energy to the valence band and conduction band of the core. As a result, the electrons reside mostly in the CdSe cores, while the holes reside mostly in the ZnTe shells. The overcoating can be a semiconductor material having a composition different from the composition of the core, and can have a band gap greater than the band gap of the core. The overcoat of a semiconductor material on a surface of the nanocrystal can include a Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

The outer surface of the nanocrystal can include a layer of compounds derived from the coordinating agent used during the growth process. The surface can be modified by repeated exposure to an excess of a competing coordinating group to form an overlayer. For example, a dispersion of the capped nanocrystal can be treated with a coordinating organic compound, such as pyridine, to produce crystals which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

Monodentate alkyl phosphines (and phosphine oxides; the term phosphine below will refer to both) can passivate nanocrystals efficiently. When nanocrystals with conventional monodentate ligands are diluted or embedded in a non-passivating environment (i.e., one where no excess ligands are present), they tend to lose their high luminescence. Typical are an abrupt decay of luminescence, aggregation, and/or phase separation. In order to overcome these limitations, polydentate ligands can be used, such as a family of polydentate oligomerized phosphine ligands. The polydentate ligands show a high affinity between ligand and nanocrystal surface. In other words, they are stronger ligands, as is expected from the chelate effect of their polydentate characteristics.

In general, a ligand for a nanocrystal can include a first monomer unit including a first moiety having affinity for a surface of the nanocrystal, a second monomer unit including a second moiety having a high water solubility, and a third monomer unit including a third moiety having a selectively reactive functional group or a selectively binding functional group. In this context, a "monomer unit" is a portion of a polymer derived from a single molecule of a monomer. For example, a monomer unit of poly(ethylene) is —$CH_2CH_2$—, and a monomer unit of poly(propylene) is —$CH_2CH(CH_3)$—. A "monomer" refers to the compound itself, prior to polymerization, e.g., ethylene is a monomer of poly(ethylene) and propylene of poly(propylene).

A selectively reactive functional group is one that can form a covalent bond with a selected reagent under selected conditions. One example of a selectively reactive functional group is a primary amine, which can react with, for example, a succinimidyl ester in water to form an amide bond. A selectively binding functional group is a functional group that can form a noncovalent complex with a selective binding counterpart. Some well known examples of selectively binding functional groups and their counterparts include biotin and streptavidin; a nucleic acid and a sequence-complementary nucleic acid; FK506 and FKBP; or an antibody and its corresponding antigen.

A moiety having high water solubility typically includes one or more ionized, ionizable, or hydrogen bonding groups, such as, for example, an amine, an alcohol, a carboxylic acid, an amide, an alkyl ether, a thiol, or other groups known in the art. Moieties that do not have high water solubility include, for example, hydrocarbyl groups such as alkyl groups or aryl groups, haloalkyl groups, and the like. High water solubility can be achieved by using multiple instances of a slightly soluble group: for example, diethyl ether is not highly water soluble, but a poly(ethylene glycol) having multiple instances of a —$CH_2$—O—$CH_2$— alkyl ether group can be highly water soluble.

For example, the ligand can include a polymer including a random copolymer. The random copolymer can be made using any method of polymerization, including cationic, anion, radical, metathesis or condensation polymerization, for example, living cationic polymerization, living anionic polymerization, ring opening metathesis polymerization, group transfer polymerization, free radical living polymerization, living Ziegler-Natta polymerization, or reversible addition fragmentation chain transfer (RAFT) polymerization. The random copolymer can include regions having each of the following formulae:

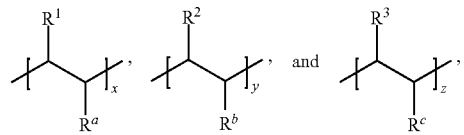

In these regions, $R^1$ is a first moiety having affinity for a surface of the nanocrystal, $R^2$ is a second moiety having a high water solubility, $R^3$ is a third moiety having a selectively reactive functional group or a selectively binding functional group, each of $R^a$, $R^b$, and $R^c$, independently, is substituted or unsubstituted alkyl, substituted or unsubstituted alkoxy, substituted or unsubstituted aryl, or substituted or unsubstituted aryloxy; and each of x, y, and z, independently, a positive integer.

In the copolymer, $x/(x+y+z)$ can be in the range of 0.1 to 0.9, $y/(x+y+z)$ can be in the range of 0.05 to 0.75, and $z/(x+y+z)$ can be in the range of 0.005 to 0.25.

A region of the formula can have of formula (I):

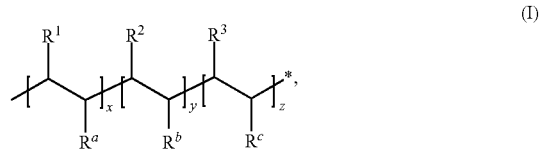

wherein each of x, y, and z, independently, is an integer selected from group consisting of 1, 2, 3, 4, 5, 6, 7, 8, 9 and 10.

In the ligand, $R^1$ can have the formula -$L^1$-$T^1$, wherein $L^1$ can be a bond or an alkylene, alkenylene, or arylene linking group having 1 to 8 chain atoms and can be optionally interrupted or terminated by —O—, —S—, —$NR^4$—, —CO—, or a combination thereof, $T^1$ can be an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, an aromatic amine moiety, or a combination thereof, and $R^4$ can be hydrogen, hydroxy, alkyl, haloalkyl, alkenyl, alkynyl, cycloalkyl, cycloalkenyl, or aryl.

In the ligand, $R^2$ can have the formula -$L^2$-$T^2$, wherein $L^2$ can be a bond or an alkylene, alkenylene, or arylene linking group having 1 to 8 chain atoms and can be optionally interrupted or terminated by —O—, —S—, —$NR^4$—, —CO—, or a combination thereof; $T^2$ can be —[O—$CH_2$—$CHR^5$]$_n$—$R^6$ wherein $R^5$ can be H or $C_1$ to $C_3$ alkyl, and $R^6$ can be H, —OH, $C_1$ to $C_6$ alkyl, $C_1$ to $C_6$ alkoxy, aryl, aryloxy, arylalkyl, or arylalkoxy, and n can be an integer in the range of 0 to 30, and $R^4$ can be hydrogen, hydroxy, alkyl, haloalkyl, alkenyl, alkynyl, cycloalkyl, cycloalkenyl, or aryl.

In the ligand, $R^3$ can have the formula -$L^3$-$T^3$, wherein $L^3$ can be a bond or an alkylene, alkenylene, or arylene linking group having 1 to 8 chain atoms and can be optionally interrupted or terminated by —O—, —S—, —$NR^4$—, —CO—, or a combination thereof, $T^3$ can be —[O—$CH_2$—$CHR^7$]$_m$—$R^8$ wherein $R^7$ can be H or $C_1$ to $C_3$ alkyl, and $R^8$ can be $C_1$ to $C_6$ aminoalkyl or $C_1$ to $C_6$ azidoalkyl, and m can be an integer in the range of 0 to 30, and $R^4$ can be hydrogen, hydroxy, alkyl, haloalkyl, alkenyl, alkynyl, cycloalkyl, cycloalkenyl, or aryl.

In the ligand, $R^1$ can have the formula -$L^1$-$T^1$, wherein $L^1$ can be a bond or an alkylene, alkenylene, or arylene linking group having 1 to 8 chain atoms and can be optionally interrupted or terminated by —O—, —S—, —$NR^4$—, —CO—, or a combination thereof, $T^1$ can be an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, an aromatic amine moiety, or a combination thereof. $R^2$ can have the formula -$L^2$-$T^2$, wherein $L^2$ can be a bond or an alkylene, alkenylene, or arylene linking group having 1 to 8 chain atoms and can be optionally interrupted or terminated by —O—, —S—, —$NR^4$—, —CO—, or a combination thereof, $T^2$ can be —[O—$CH_2$—$CHR^5$]$_n$—$R^6$ wherein $R^5$ can be H or $C_1$ to $C_3$ alkyl, and $R^6$ can be H, —OH, $C_1$ to $C_6$ alkyl, $C_1$ to $C_6$ alkoxy, aryl, aryloxy, arylalkyl, or arylalkoxy, and n can be an integer in the range of 0 to 30. And, $R^3$ can have the formula -$L^3$-$T^3$, wherein $L^3$ can be a bond or an alkylene, alkenylene, or arylene linking group having 1 to 8 chain atoms and can be optionally interrupted or terminated by —O—, —S—, —$NR^4$—, —CO—, or a combination thereof, $T^3$ can be —[O—$CH_2$—$CHR^7$]$_m$—$R^8$ wherein $R^7$ can be H or $C_1$ to $C_3$ alkyl; and $R^8$ can be $C_1$ to $C_6$ aminoalkyl or $C_1$ to $C_6$ azidoalkyl, and m can be an integer in the range of 0 to 30, and each $R^4$, independently, can be hydrogen, hydroxy, alkyl, haloalkyl, alkenyl, alkynyl, cycloalkyl, cycloalkenyl, or aryl.

In the ligand, $L^1$, $L^2$, and $L^3$ can be each independently —C(O)NH—$(CH_2)_i$— wherein i is an integer in the range of 0 to 6. $T^1$ can be an imidazolyl moiety. $T^2$ can be —[O—$CH_2$—$CH_2$]$_n$—$OR^6$ wherein n can be an integer in the range of 5 to 25 and $R^6$ can be H, methyl, or ethyl. $T^3$ can be —[O—$CH_2$—$CH_2$]$_m$—$R^8$ wherein $R^8$ is $C_1$ to $C_6$ aminoalkyl or $C_1$ to $C_6$ azidoalkyl, and m can be an integer in the range of 0 to 10.

Polyhistidine motifs can have high affinity a nanocrystal surface (e.g., when the surface includes Cd and/or Zn, or other Group II elements), and $His_6$-tags have been employed for facile and efficient derivatization of nanocrystals with peptides, dyes, and proteins. See, for example, Howarth, M. et al. *Nat Meth* 2008, 5, (5), 397-399; Sapsford, K. E. et al. *J. Phys. Chem. C.* 2007, 111, (11528-11538); Medintz, I. L. et al. *Bioconjugate Chemistry* 2008, 19, (9), 1785-1795; and Aaron R. Clapp, et al. *ChemPhysChem* 2006, 7, (1), 47-57, each of which is incorporated by reference in its entirety.

A polymer rich with imidazole groups can achieve efficient and multi-dentate binding to a nanocrystal surface. The polyimidazole motif can be advantageous because it is not susceptible to the issues plaguing thiol-based chemistry, such as degradation by oxidation. Furthermore, multidentate binding by a polyhistidine can greatly enhance stability. See, for example, Yildiz, I. et al. *Langmuir* 2009, 25, (12), 7090-7096, which is incorporated by reference in its entirety. To promote water solubility and reduce non-specific binding, a PEG derived monomer can be co-polymerized along with an imidazole-based monomer to form a co-polymer displaying both PEG and imidazole groups along the backbone. See, for example, Bentzen, E. L. et al. *Bioconjugate Chemistry* 2005, 16, (6), 1488-1494, which is incorporated by reference in its entirety. Using an additional monomer featuring an amine or a biotin functional group, a 3-component multi-functional co-polymer can be synthesized for nanocrystal water solubilization and derivatization.

Radical addition fragmentation chain transfer (RAFT) polymerization chemistry can provide molecular weight control and narrow polydispersity of the co-polymer. The RAFT agent can also mediate polymerization of a wide diversity of monomers for controlled copolymerization. See, for example, Chiefari, J. et al. *Macromolecules* 1998, 31, (16), 5559-5562, which is incorporated by reference in its entirety. By tuning the ratio and composition of monomers, complex co-polymers can be assembled with the desired properties for nanocrystal water solubilization and derivatization, form compact nanocrystals suitable for live cell and in-vivo imaging with extremely low non-specific binding and greatly enhanced stability and long-term shelf-life. By using a catechol group instead of imidazole for binding, iron oxide nanocrystals can also be solublized. The length of PEG chain can be chosen in part based on the size of the nanocrystal involved-larger nanocrystals can require longer PEG chains for solubility.

Figure 7:
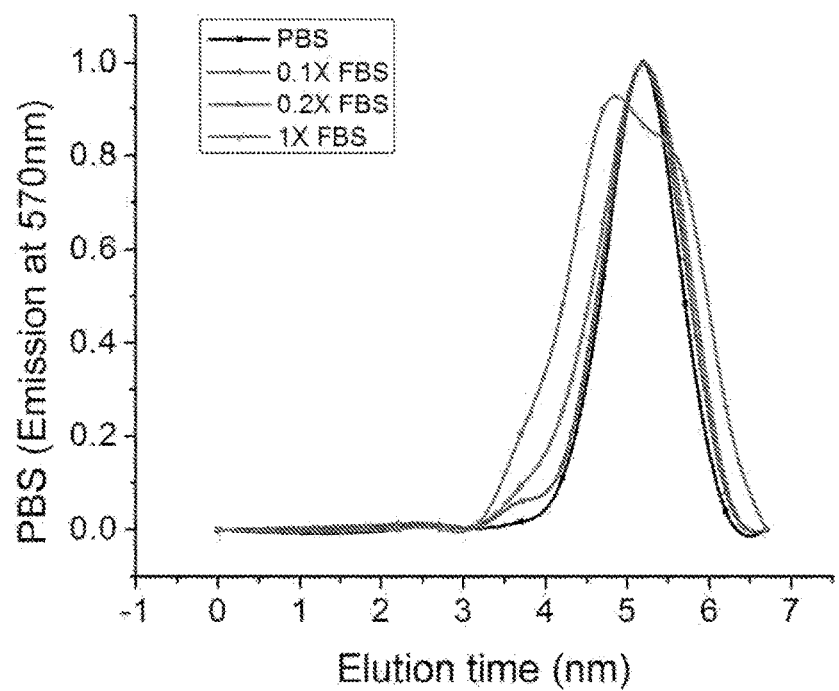
FIG. 7 is an example of size exclusion chromatogram with fluorescence detection of a serum binding test for typical sulfonate betaine PIL coated nanocrystals.
Figure 8:
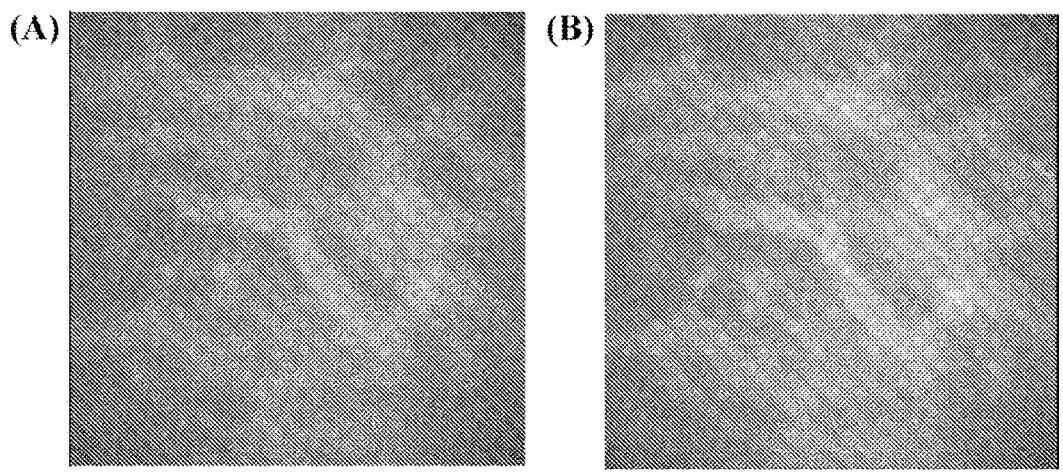
FIG. 8 is in vivo images of the extravasation of SBPIL coated nanocrystals from microvessels into tumor at (A) 10 min post injection and (B) 60 min post injection.

The betaine PIL coated semiconductor nanocrystals can exhibit low non-specific binding to cells, proteins, and the in vitro environment of the in vitro labeling experiment. The protein can be a receptor on the surface of the cell or a protein within the cell in the cytoplasm. FIG. 7 shows low non-specific binding to proteins and serum. FIG. 8 shows low non-specific binding to cells.

Examples

Synthesis of CdSe(CdS)

CdSe core with 480 nm first absorption peak was synthesized using a previously reported method. See, for example, Peng, Z. A.; Peng, X. *J. Am. Chem. Soc.* 2001, 123, 183-184, which is incorporated by reference in its entirety. To summarize, 0.4 mmol (54.1 mg) of CdO, 0.8 mmol (0.2232 g) of TDPA, 9.6 mmol (3.72 g) of TOPO were placed in 25 mL round bottom flask. The solution was degassed for 1 hr at 160° C. and heated to 300° C. under argon until CdO dissolved and formed clear homogenous solution and was followed by pulling vacuum at 160° C. to remove evolved water. The solution was reheated to 360° C. under argon and TBP-Se solution (1.5 mL of 1.5 M TBP-Se in 1.5 mL of TOP) was rapidly added to give CdSe cores with the first absorption feature at 468 nm. The core was grown at 260° C. to produce the core with the desired wavelength.

CdS shells were deposited on CdSe core via modification of previously reported procedures. See, for example, Liu, W. et al. *J. Am. Chem. Soc.* 2010, 132, 472-483, which is incorporated by reference in its entirety. Cores isolated by repeated precipitations from hexane with acetone were brought to 180° C. in a solvent mixture of oleylamine (3 mL) and octadecene (6 mL). Aliquots of Cd and S precursor solutions were then introduced alternately starting with the metal (Cd) and waiting 15 min between the start of each addition. The Cd precursor consisted of 0.33 mmol Cd-oleate and 0.66 mmol oleylamine in a solvent mixture of octadecene (1.5 mL) and TOP (3 mL). The S precursor consisted of 0.3 mmol hexamethyldisilathiane [$(TMS)_2S$] in 6 mL TOP. The dose of each overcoating precursor aliquot corresponds a single monolayer of ions to the nanocrystal surface. Addition of a total of 4 aliquots each of Cd and S yielded nanocrystal with emission at 570 nm and quantum yield close to unity when diluted in octane. A similar procedure was performed on larger CdSe cores to obtain CdSe(CdS) nanocrystals emitting at 605 nm. See, for example, Snee, P. T. et al. *Adv. Mater.* 2005, 17, 1131-1136; and Leatherdale, C. A. et al. *J. Phys. Chem. B.* 2002, 106, 7619-7622, each of which is incorporated by reference in its entirety. The extinction coefficient of CdSe(CdS) was calculated using the extinction coefficient of CdSe core from literature and assuming that 100% of CdSe cores were retained for the overcoating step. See, for example, Leatherdale, C. A. et al. *J. Phys. Chem. B.* 2002, 106, 7619-7622, which is incorporated by reference in its entirety.

Monomer Synthesis and Polymerization

All monomers were kept as dilute stock solutions between 30-100 mg/mL in ethylacetate. Stock solutions of RAFT agent (using dibenzyl carbonotrithioate) were prepared at 220 mg/mL in DMF, and AIBN was prepared at 50 mg/mL in DMF. All reagents were weighed out volumetrically. In a typical polymerization, monomers 1 (35.5 mg, 0.25 mmol) and 3 (66.3 mg, 0.25 mmol) were added to an 8 mL vial. The solvent was removed in vacuo and 50 µL of dry DMF along with RAFT agent (2.63 mg, 0.0125 mmol), and AIBN (2.05 mg, 0.0125 mmol) were added. The contents of the vial were mixed, centrifuged at 5000×g for 2 min, and then transferred to a 1 mL ampule. The ampule was subjected to 4 cycles of freeze-pump-thaw, and sealed under vacuum using a butane torch. The vial was heated to 70° C. on an oil bath for 3.5 h. Aliquot of the polymer solution was analyzed using GPC to determine molecular weight and polydispersity. After confirming the polymerization was complete, the polymer solution was transferred to a 8 mL vial, which was followed by addition of anhydrous THF (2 mL) and either 1,3-propane sultone (33.6 mg, 0.275 mmol) or β-propiolactone (23.8 mg, 0.275 mmol). Gelation occurred within 6 h but the reaction solution was stirred 24 hours. THF was removed in vacuo and 0.5 mL of a 4 M solution of HCl in MeOH was added to cleave the Boc protecting groups. After 1 h at RT, the HCl was removed in vacuo. The deprotected polymer was dissolved in MeOH, to which a solution of NaOH in $H_2O$ (5 M) was added dropwise to adjust the pH to be between 9 and 10. The solvent was removed in vacuo, and then 2,2,2-trifluoroethanol was added to precipitate the salts. The solution was filtered through a 0.45 µm PTFE filter and the solvent removed in vacuo to yield the final polymer for ligand exchange.

Compound 1

N,N-dimethyl ethylene diamine (3.17 g, 36 mmol) was added to an anhydrous THF (60 mL) at 4° C. To this solution, acryloyl chloride (2.70 g, 30 mmol) was injected slowly which is followed by addition of triethylamine (3.64 g, 36 mmol). The solution was warmed to room temperature and stirred for 2 h. Precipitates were removed by filtration, and the solvent was evaporated in vacuo. Ethylacetate (50 mL) was added to facilitate further precipitation of reaction byproducts, and the solution was filtered once more. The crude product was purified by silica column (ethyl acetate/hexanes gradient 50:50 to 100:0, v/v) to give the pure product as a clear oil (2.59 g, 72% yield). $^1$H NMR (400 MHz, $CDCl_3$): δ (ppm) 6.19 (dd, J1) 1.8 Hz, J2=17.0 Hz, 1H), 6.07 (dd, J1=9.8 Hz, J2=17.0 Hz, 1H), 5.53 (dd, J1=1.8 Hz, J2=10.0 Hz, 1H), 3.38 (dt, J1=5.6 Hz, J2=5.6 Hz, 2H), 2.41 (t, 2H), 2.20 (s, 6H).

Compound 2

To a stirred solution of acrylic acid (1.00 g, 13.88 mmol) and N-hydroxysuccinimide (NHS) (1.91 g, 16.65 mmol) in 40 mL of dry THF was added dropwise a solution of dicyclohexylcarbodiimide (DCC) (3.43 g, 16.65 mmol) in 10 mL dry THF with stirring at 4° C. The solution was warmed to room temperature and stirred for 2 h. Precipitates were removed by filtration, and the solvent was evaporated in vacuo. Ethylacetate (50 mL) was added to facilitate further precipitation of reaction byproducts, and the solution was filtered once more. The solvent was evaporated and the product dissolved in either 10 mL of anhydrous DMF or dry THF to create a stock solution, which was used in later reaction steps without further purification.

Compound 3

To an aqueous solution of sodium bicarbonate (50 mL, 0.3 M) was added DMF (50 mL) and histamine dihydrochloride (2.50 g, 13.59 mmol). To this solution was added compound 2 (2.75 g, 16.3 mmol) in a solution of DMF, with stirring at 4° C. The reaction was monitored via TLC by ninhydrin stain for primary amines, and confirmed to be complete after 30 min to give the crude compound 3. The solvent was removed in vacuo, and the product redissolved in DMF (50 mL). The solution was filtered, and triethylamine was introduced (2.27 mL, 16.30 mmol). Ditert-butyl dicarbonate was added dropwise at 4° C., and the solution was stirred overnight at RT. Water was added and the solution extracted with $CHCl_3$ (3×25 mL). The organics were combined and dried over sodium sulfate, and the solvent removed in vacuo. The crude product was purified by silica column (ethyl acetate/hexanes gradient 50:50 to 100:0, v/v) to give the pure product as a clear oil (2.59 g, 72% yield). $^1$H NMR (400 MHz, $CDCl_3$): δ (ppm) 7.95 (s, 1H), 7.10 (s, 1H), 6.19 (dd, J1) 1.8 Hz, J2) 17.0 Hz, 1H), 6.07 (dd, J1) 9.8 Hz, J2) 17.0 Hz, 1H), 5.53 (dd, J1) 1.8 Hz, J2) 10.0 Hz, 1H), 3.53 (dt, 2H), 2.72 (t, 2H), 1.54 (s, 9H).

Figure 2:
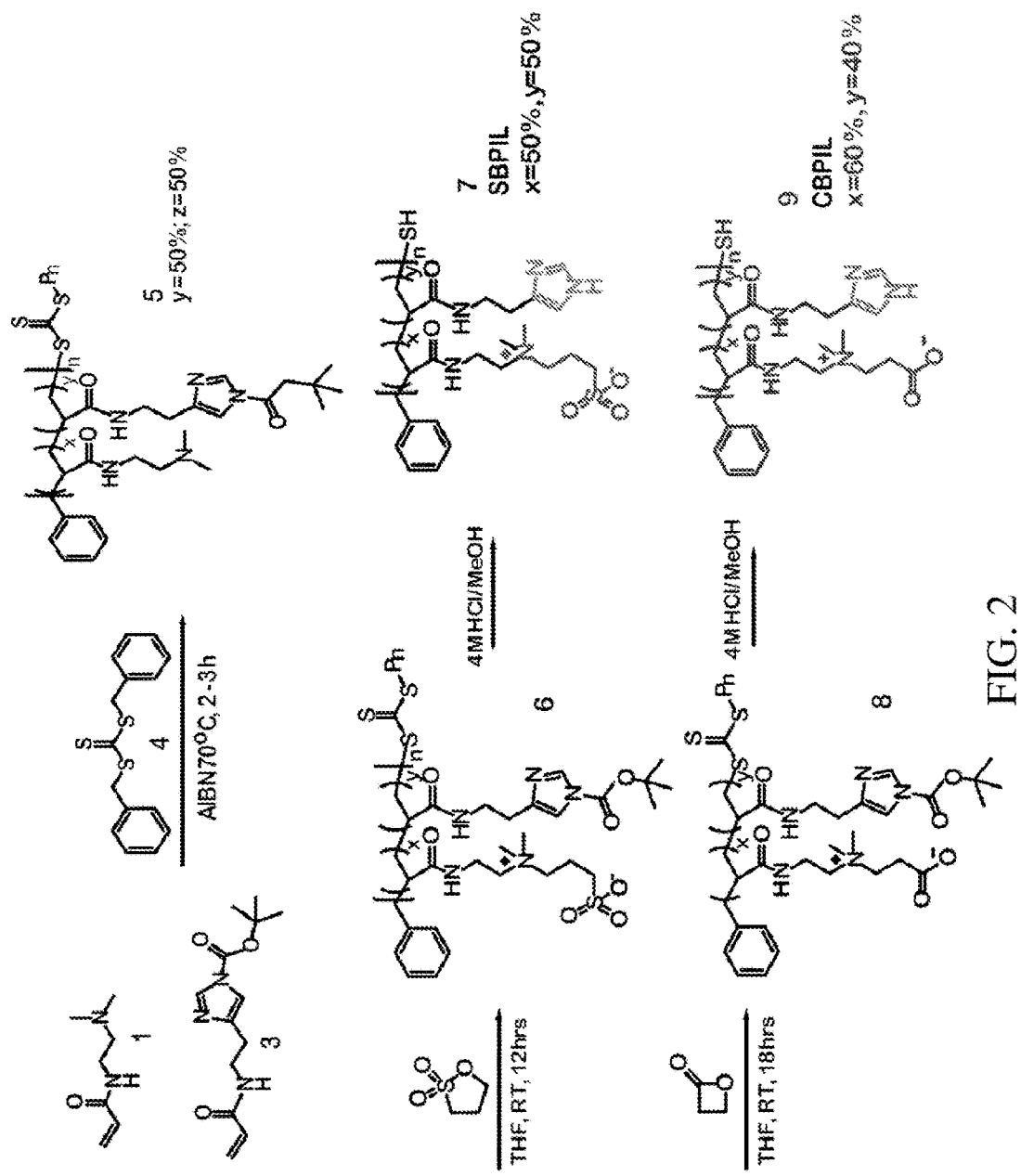
FIG. 2 is a schematic of the synthesis of betaine poly imidazole ligands (PILs).

The synthesis of betaine PILs involved three steps (FIG. 2). (1) RAFT mediated polymerization of backbone (Polymer 5), (2) betainisation of the polymers (Polymer 6, 8) and (3) cleavage of BOC protecting groups (Polymer 7, 9). Post modification of a polymerized backbone to yield betaine PILs was chosen as pre-modified zwitterionic monomer exhibited very limited solubility in organic solvents.

Figure 5:
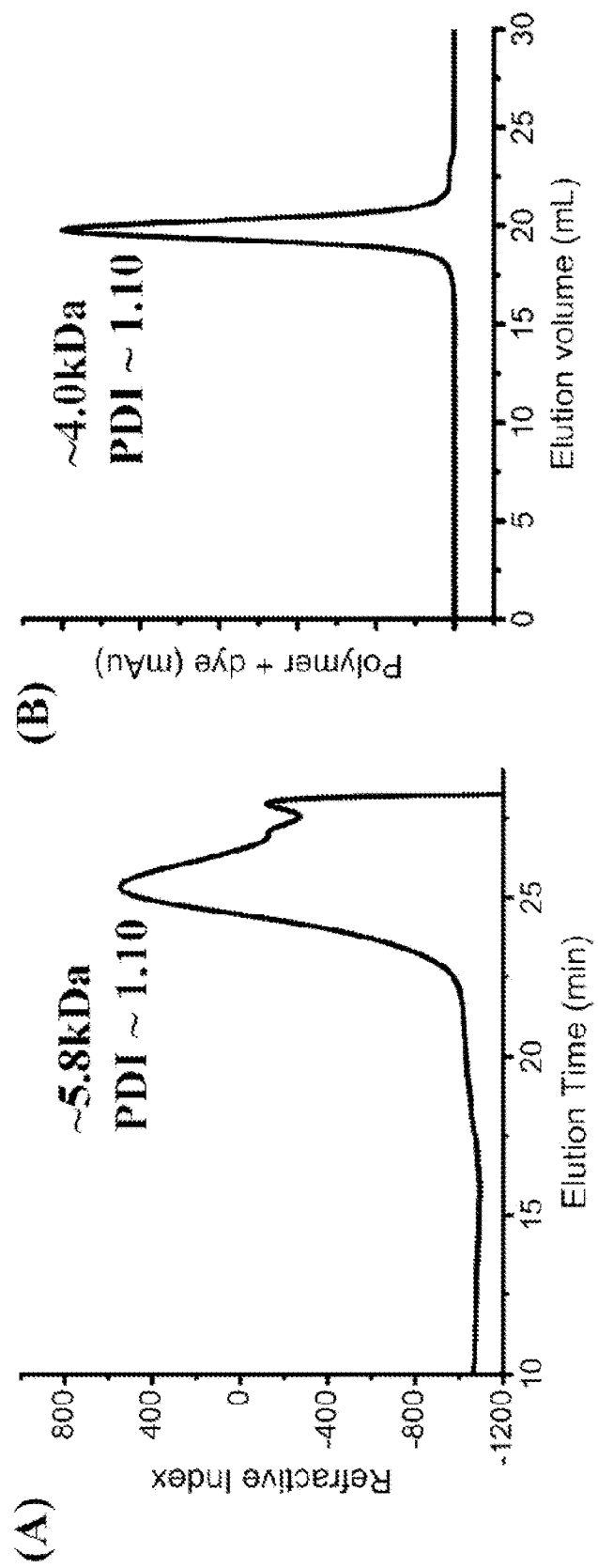
FIG. 5 is an example of (A) gel permeation chromatogram and (B) gel filtration chromatogram of typical betain polymers.

To prepare the monomer, N-hydroxysuccinimide actived acrylic acid or acryloyl chloride was coupled to primary amine containing moieties (histamine and N,N-dimethyl diethane 1,2 diamine) and purified using a silica column (FIG. 1). The purified monomers were polymerized via RAFT mediated polymerization using dibenzyl carbonotrithioate as a RAFT reagent and azobisisobutyronitrile (AIBN) as an initiator in dry DMF (FIG. 2). The resulting polymer (polymer 5) was used for betainisation without further purification. Before the betainisation, the polymers were soluble in DMF which allowed characterization of the molecular weight and the polydispersity of the polymer samples by gel permeation chromatography (GPC) on polystyrene beads (FIG. 5A).

For betainisation, highly strained 1,3-sultone and β-propiolactone were used. Release of ring strain allowed one-step and quantitative conversion of tertiary amine to quaternary amine and either sulfonate (sulfonate betaine PIL (SBPIL), Polymer 7) or carboxylate group (carboxylate betaine PIL (CBPIL), Polymer 9). Briefly, 1,3-propanesultone or β-propiolactone (in 10 mol % excess based on 2-(dimethylamino)ethyl acrylate residues) was added to polymer 5 in anhydrous THF. After stirring the solution for 24 hrs at room temperature, the solution was centrifuged and the supernatant was discarded. The pellet was washed with THF three more times to remove unreacted 1,3-propanesultone or β-propiolactone. The extent of the betainisation was calculated using $^1$H NMR. Due to the peak broadening in polymer samples and the peaks being close to each other in case of Polymer 5, 6, and 8, the extent of betainisation was measured for a 2-(dimethylamino)ethyl acrylate homopolymer sample to anticipate the conversion efficiencies for the betaine PILs (conversion efficiency~100%). After the betainisation, the polymers were only soluble in highly fluorinated organic solvents such as 2,2,2-trifluoroethanol and 1,1,1,3,3,3-hexafluoropropan-2ol or aqueous solution. Therefore, the characterization of the final polymers was achieved using gel filtration chromatography against protein standards (BioRad) (FIG. 5B). The narrow molecular mass distribution of polymer 5 was retained even after the betainisation which also showed that conversion efficiencies of tertiary amine to the betaine moieties were almost unity. Lower apparent molecular weight of the final polymer (polymer 7, 9) than that of the polymer before the betainisation (polymer 5) might be due to their hydrodynamic volume of the betaine PILs being different to proteins used as standards (Vitamin $B_{12}$, myoglobin, Ovalbumin, and gamma globulin). Other examples of the synthesis include the following:

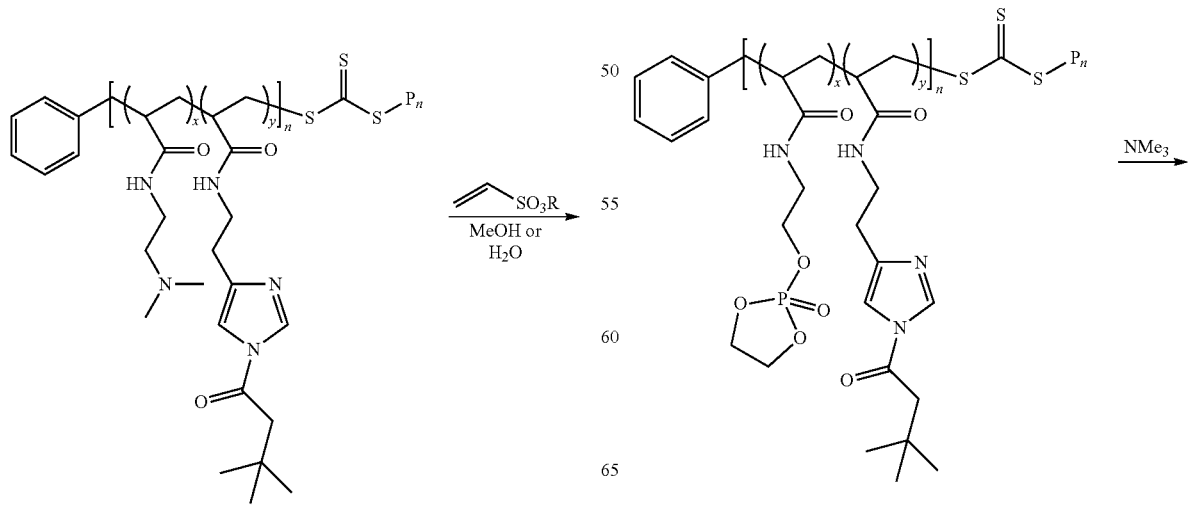

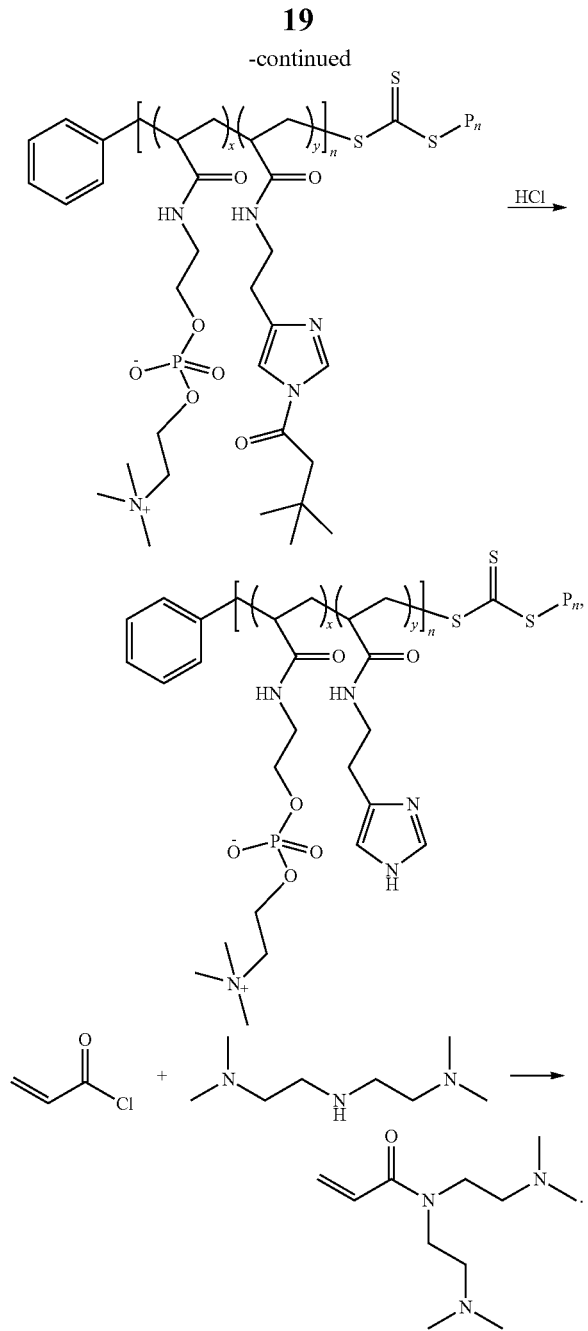

Ligand Exchange and Characterization of Aqueous Nanocrystals

Figure 3:
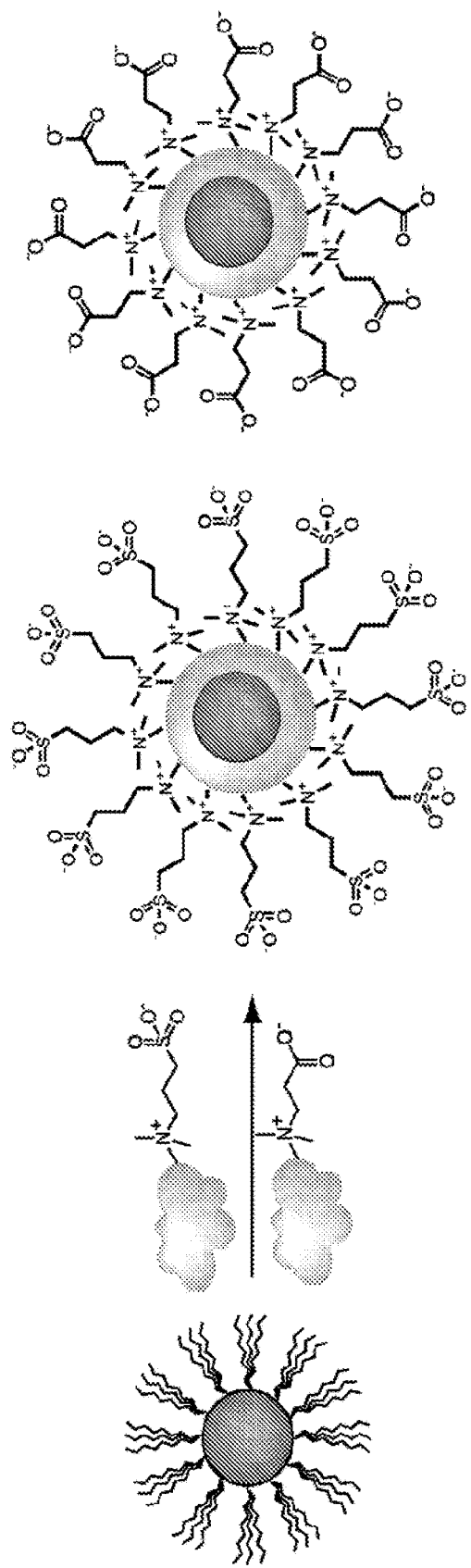
FIG. 3 is a schematic representation of ligand exchange with the betaine PILs.
Figure 6:
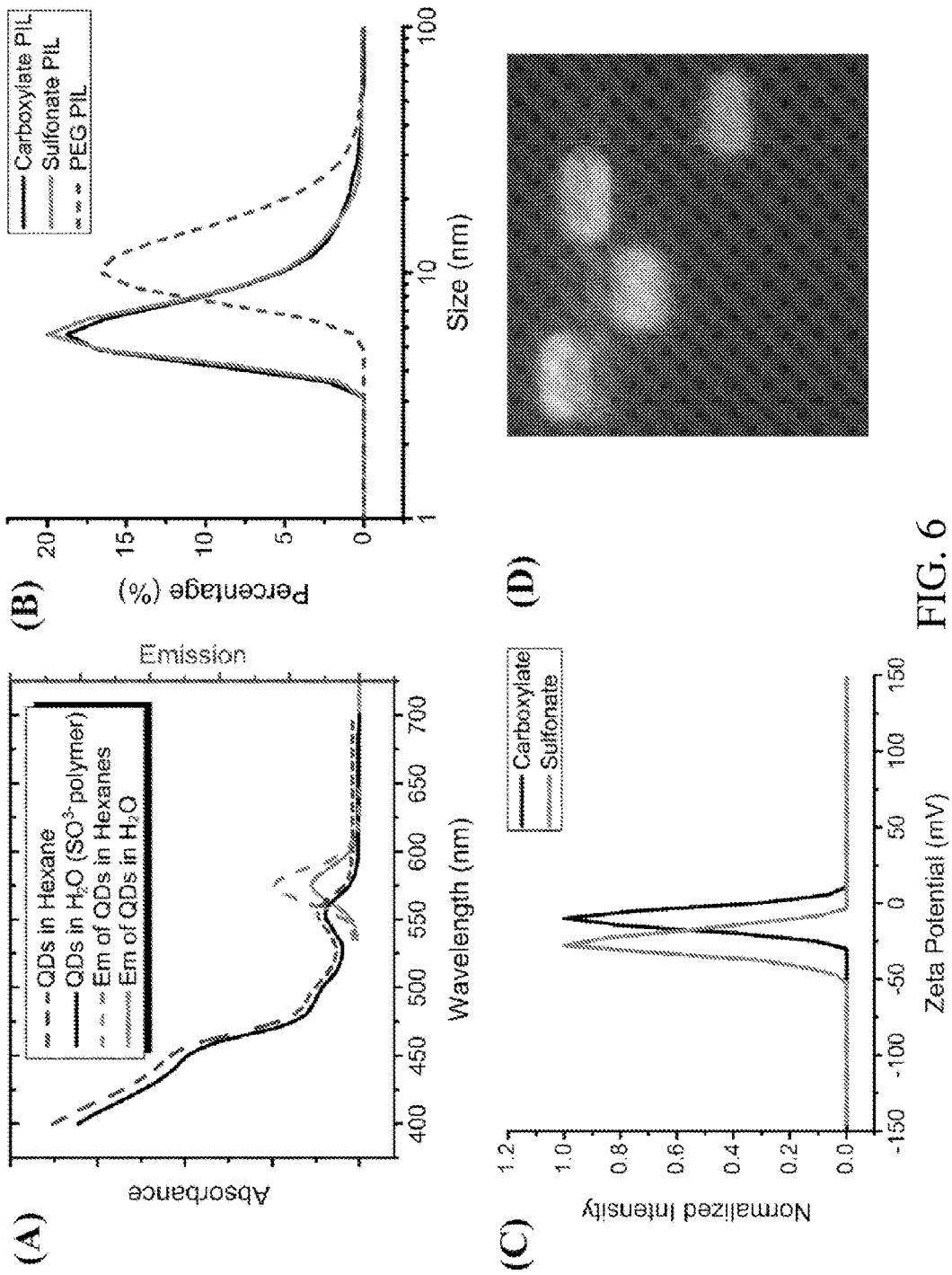
FIG. 6 is an example of (A) absorption (solid black and dashed blue lines) and emission (solid red and dashed green lines) spectra of the betaine PILs coated nanocrystals before (dashed) and after (solid) ligand exchange with SBPILs; (B) the dynamic light scattering data of SBPIL-coated, CBPIL-coated, and PEG PIL-coated nanocrystals; (C) the zeta potential for SBPIL-coated and CBPIL-coated nanocrystals; and (D) gel electrophoresis analysis of the SBPIL-coated and CBPIL-coated nanocrystals.

Water soluble nanocrystals coated with the betaine PIL was prepared by ligand exchange of the native hydrophobic ligand capped CdSe(CdS) core(shell) nanocrystals with imidazole rings along the polymer backbone (FIG. 3). InAs $(Cd_xZn_{1-x}S)$ emitting at 800 nm and CdSe(CdS) emitting at 570 nm and 605 nm were used for ligand exchange. The betaine PILs in 2,2,2-trifluoroethanol was added dropwise to nanocrystals in THF. Slow addition of the polymer solution is very important to allow time for nanocrystals to be ligand exchanged with the polymer to prevent nanocrystals from being precipitated when 2,2,2-trifluoroethanol is added to THF. After 1 h of stirring, nanocrystals were precipitated with excess hexane and re-dispersed in 1× phosphate buffer saline (PBS) followed by three times of dialysis to get rid of excess polymers. Both InAs$(Cd_xZn_{1-x}S)$ and CdSe(CdS) were successfully ligand exchanged and dispersed in PBS without aggregation according to GFC. Absorbance and Emission spectra of CdSe(CdS) before and after the ligand exchange are shown in FIG. 6A. Quantum yield (QY) of CdSe(CdS) showed a modest drop from >90% (in octane with native coatings) down to 55% after the ligand exchange. PEG PIL coated nanocrystals showed slightly higher QY (~65%) than betaine PIL coated nanocrystals (~55%). See, for example, Liu, W. et al. *J. Am. Chem. Soc.* 2010, 132, 472-483, which is incorporated by reference in its entirety. This may be due to better passivation of nanocrystal surface in case of PEG PILs with their long repeating units of ethylene glycol. Absorption and emission features can change depending on which semiconductor nanocrystals are chosen. The absolute number for hydrodynamic diameter and zeta potential can also change depending on the size of the semiconductor nanocrystals. Semiconductor nanocrystals with a 3.5 nm inorganic core diameter (very small core) and a PEG PIL coat, the hydrodynamic diameter of the PEG PIL coated semiconductor nanocrystals becomes ~9-10 nm. The PEG PIL adds 6~7 nm in hydrodynamic diameter from original inorganic size. Semiconductor nanocrystals with the same core (3.5 nm), but with a betaine PIL coat, the hydrodynamic diameter of the betaine PIL coated semiconductor nanocrystals becomes ~7-8 nm in hydrodynamic diameter which means betaine PIL adds 3-4 nm in hydrodynamic diameter. Betaine PIL provides smaller, more compact, semiconductor nanocrystals than PEG PILs.

Figure 9:
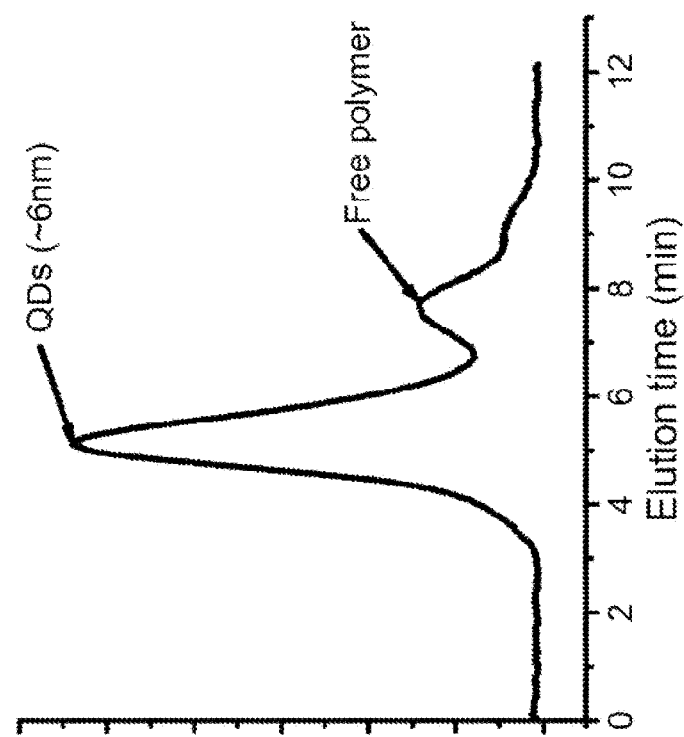
FIG. 9 is an example of (A) TEM image and (B) gel filtration chromatogram after the ligand exchange.
Figure 9:
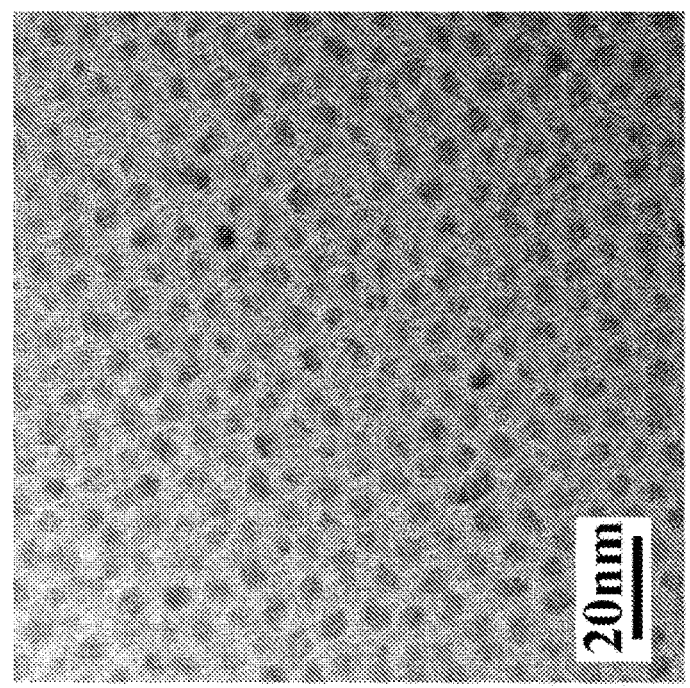

GFC traces and TEM images after the ligand exchange show non-aggregated monodisperse samples (FIG. 9). The hydrodynamic diameter of the betain PILs coated nanocrystals were significantly smaller (~6 nm by gel filtration chromatography, ~7 nm by dynamic light scattering) than that of PEG PIL coated nanocrystals (~11 nm) (FIG. 6B). Small size of the nanocrystal construct can be beneficial for efficient FRET for energy transfer sensing applications and the access of the nanocrystal constructs to crowed biological regions such as neuronal synapses. In addition, it has been shown that nanocrystals smaller than 5.5 nm in hydrodynamic diameter can be cleared via urinary excretion as intact nanoparticles for nanocrystal applications in vivo. See, for example, Choi, H. S. et al. *Nat. Biotech.* 2007, 25, 1165-70, which is incorporated by reference in its entirety. GFC was performed only for SBPIL coated nanocrystals as the interaction of CBPIL coated nanocrystals with GFC media prevented the illusion of the particles. However, DLS data showed the hydrodynamic diameter of the CBPIL coated nanocrystals is very similar as that of the SBPIL coated nanocrystals.

The surface charge of SBPILs coated nanocrystals and CBPILs coated nanocrystals were characterized by measuring the zeta potential and performing gel electrophoresis. Zeta potential for SBPILs was ~−26 mV (mildly negatively charged) and that for CBPILs was ~−10 mV (close to neutral) (FIG. 6C). This data is consistent with the gel electrophoresis results where nanocrystals coated with CBPILs did not move during the gel electrophoresis while nanocrystals coated with SBPILs moved slightly towards a positive electrode (FIG. 6D). PEG PILs coated nanocrystals (close to neutral) and dihydrolipoic acid (DHLA) coated nanocrystals (highly negatively charged) were run with the betaine PILs coated nanocrystals as control. SBPILs coated nanocrystals appeared slightly negatively charged by gel electrophoresis. This extra charge, despite the zwitteronic nature of the ligand system, can be explained by the fact that quaternary amine can be associated with negative ions in buffer which screens the positive charge of the amine.

However, in case of CBPILs, quaternary amine was separated from carboxylate with only two carbons (as opposed to three carbons in case of SBPILs) and might not have enough space for a negative ion to be associated between quaternary amine and carboxylic acid.

Conjugation to an Energy Transfer Dye

Figure 4:
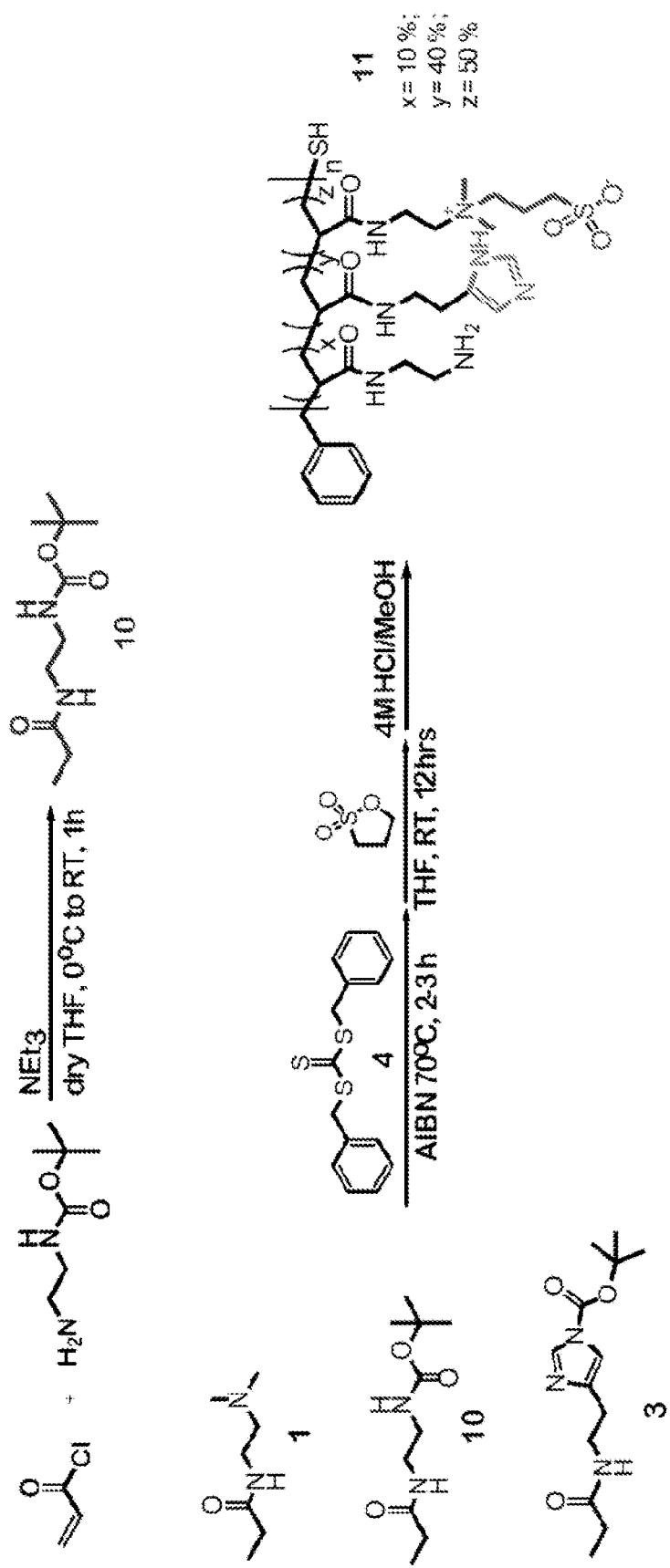
FIG. 4 is a schematic of the synthesis of betaine poly imidazole ligands (PILs).

With exceptionally small hydrodynamic diameter of the SBPIL coated nanocrystals, highly efficient FRET can be expected for nanocrystal-dye conjugates. To conjugate dyes to nanocrystals, primary amine monomer (monomer 10) was incorporated to the polymer (FIG. 4, polymer 11) and the amine group was coupled to NHS activated Alexa 594.

Serum Binding Test and In Vivo Imaging

Since zwitterionic SAMs, betaine polymer coated silica particles and gold nanoparticles have shown very low non-specific adsorption of proteins in previous studies, betaine PIL coated nanocrystals were also expected to display very low bio-fouling property. See, for example, Holmlin, R. E. et al. *Langmuir* 2001, 17, 2841-2850; Chen, S. et al. *J. Am. Chem. Soc.* 2005, 127, 14473-14478; Ladd, J. et al. *Biomacromolecules* 2008, 9, 1357-1361; Jia, G. et al. *Langmuir* 2009, 25, 3196-3199, each of which is incorporated by reference in its entirety. To illustrate the stability of the nanocrystals for in vivo imaging experiments, the SBPIL coated nanocrystals were incubated with 1×PBS, 0.1× fetal bovine serum (FBS), 0.2×FBS and 1×FBS. The size change of the nanocrystals before and after the incubation was verified using size exclusion chromatography with fluorescence detection. Nanocrystals coated with SBPILs exhibited negligible non-specific protein binding after the incubation with PBS, 0.1×FBS and 0.2×FBS and low protein binding when incubated with 1×FBS (FIG. 7).

Probing Microenvironment of the Tumor Using SBPIL Coated InAs

With low non-specific protein binding of SBPIL coated nanocrystals and the high permeability of tumor vessels, the extravasation of the nanocrystals from micro vessels into the tumor was imaged. Using a breast tumor model grown beneath transparent windows in mice, vascular transport of nanocrystals after intravenous injection was imaged via two-photon laser scanning microscopy as a function of time to measure the diffusion rate of the nanocrystals. InAs ($Cd_xZn_{1-x}S$) SBPILs nanocrystals emitting at 800 nm were injected retro-orbitally, and the tumor vasculature was imaged over 1 h. Initially, the nanocrystals are confined within the microvessels (FIG. 8A). See, for example, Jain, R. K. et al. *Nat Rev Cancer* 2002, 2, 266-276; Jain, R. K. et al. *In Live Cell Imaging: A Laboratory Manual*; Cold Spring Harbor Laboratory Press: Cold Spring Harbor, N.Y., 2004, p 435-66; Huang, P.; et al. *J. Am. Chem. Soc.* 2008, 47, 170-170. After 1 h, brightening of the vessels due to the extravasation of nanocrystals into tumor was observed (FIG. 8B). During the experiments, the nanocrystals were stable and did not aggregate on the vessel walls, which indicated a strong potential of SBPIL coated nanocrystals for further in vivo studies.

Imaging can also be done using one-photon imaging. Two-photon imaging can be used because background autofluorescence became significantly lower for two-photon imaging. Also, the coated semiconductor nanocrystals can also be used in diffusion studies or targeting studies where tumors, organs, cells, macromolecules, etc, can be targeted.

In vitro imaging experiments can include labeling receptors on the cell surfaces or protein labeling in cytoplasm. The experiments can include sensing analytes inside cells with sensors derivatized from betaine PIL type ligands.

Materials and Instrumentation

All chemicals unless indicated were obtained from Sigma Aldrich and used as received. Air sensitive materials were handled in an Omni-Lab VAC glovebox under dry nitrogen atmosphere with oxygen levels <0.2 ppm. All solvents were spectrophotometric grade and purchased from EMD Biosciences. Amine-bearing compounds were visualized on thin layer chromatography (TLC) plates using a ninhydrin solution. Acrylate compounds bearing terminal vinyl groups were visualized on TLC using $KMnO_4$. All other TLC plates were visualized by iodine staining. Flash column chromatography was performed on a Teledyne Isco CombiFlash Companion. $^1H$ NMR spectra were recorded on a Bruker DRX 401 NMR Spectrometer. UV-vis absorbance spectra were taken using an HP 8453 diode array spectrophotometer. Photoluminescence and absorbance spectra were recorded with a BioTek Synergy 4 Microplate Reader. Dynamic light scattering analysis was performed on a Malvern Instruments ZetaSizer ZS90 in a low volume 12 µL quartz cuvette, with nanocrystal concentrations between 1-3 µM. Molecular weights of polymers before betainisation were determined in DMF solutions on an ÄKTAprime Plus chromatography system from Amersham Biosciences equipped with a self-packed Superose 12 10/300 column against BioRad Gel filtration standards.

Gel Filtration Chromatography (GFC)

GFC was performed using an ÄKTAprime Plus chromatography system from Amersham Biosciences equipped with a self-packed Superdex 200 10/100 column or Superose 6 10/300 column (to characterize nanocrystals after ligand exchange) or Superose 12 10/300 column (to characterize betaine PILs). PBS (pH 7.4) was used as the mobile phase with a flow rate of 1.0 mL/min for Supersex 200 and Superose 12 or 0.5 mL/min for Superose 6. Typical injection volume was 100 µL. Detection was achieved by measuring the absorption at 280 nm.

Animal and Tumor Models

Orthotopic P008 mammary carcinoma models were prepared by implanting a small piece (1 $mm^3$) of viable tumor tissue from the source tumor animal into the mammary fat pad of 10-12-week old female Tie2-GFP/FVB mice. The tumors were allowed to grow up to 5 mm in diameter. All animal procedures were carried out following the Public Health Service Policy on Humane Care of Laboratory Animals and approved by the Institutional Animal Care and Use Committee of Massachusetts General Hospital.

Intravital Multiphoton Imaging

To study tumor vasculature using nanocrystals and their distribution dynamic in live animals, 150 µL poly(PEG)-PIL nanocrystal 600 at a concentration of 5 µM were injected retro-orbitally into the tumor bearing mice and imaged with multiphoton laser scanning microscope. The images were recorded as 3D stacks (200-µm thickness, 1-µm step size) at 0 h, 3 and 6 h interval respectively and processed using the NIH ImageJ software. For the GFP channel, the emission filter used was 535 (20 nm, and for NC600, the emission filter was 625 (75 nm. All images were captured with a 20× water emersion lens (N.A. 0.95) and an excitation wavelength of 880 nm (500 mW).

Measurement of Quantum Yield (QY)

Figure 10:
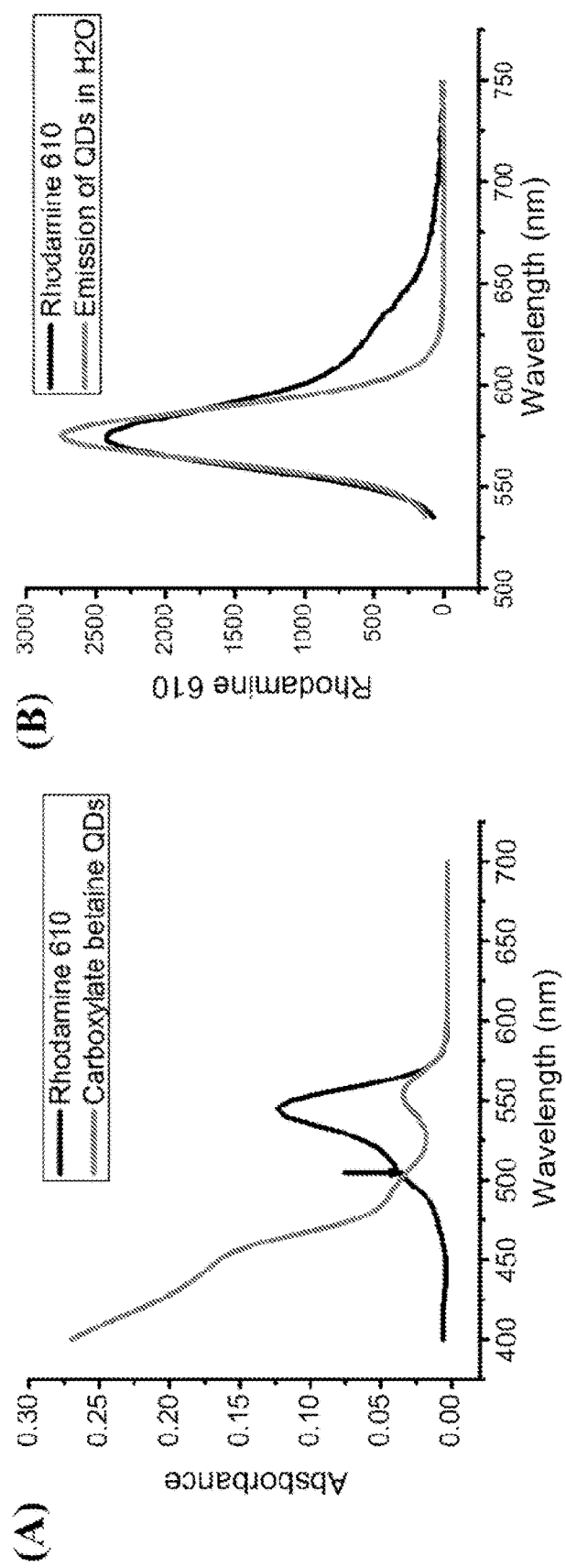
FIG. 10 shows a method to measure the QY of CBPIL-coated nanocrystals relative to Rhodamine 610. First, (A) matches the optical density of the semiconductor nanocrystals sample to Rhodamine 610 at the excitation wavelength and (B) measures the ratio of emission intensity between the semiconductor nanocrystals and the Rhodamine 610 sample.

The QY of nanocrystal 570 was measured relative to Rhodamine 610 (QY 68% in ethanol) with excitation at 505 nm and QY of nanocrystal 605 was measured relative to Rhodamine 640 (QY 100% in ethanol with excitation at 535 nm) (FIG. 10). Solutions of nanocrystals in octane (native CdSe/CdS nanocrystals) or PBS (nanocrystals after ligand exchanged with betaine PILs) and dye in ethanol were optically matched at the excitation wavelength. Fluorescence spectra of nanocrystal and dye were taken under identical spectrometer conditions in quadruplicate and averaged. The optical density was kept below 0.1 at the $\lambda_{max}$, and the integrated intensities of the emission spectra, corrected for differences in index of refraction and concentration, were used to calculate the quantum yields using the expression $QY_{NC}=(Absorbance)_{dye}/(Absorbance)_{NC} \times (Peak\ Area)_{NC}/(Peak\ Area)_{Dye} \times (n_{NC solvent})^2/(n_{Dye\ solvent})^2 \times QY_{Dye}$.

Agarose Gel Electrophoresis

Electrophoresis of nanocrystals was performed using a OWL B 1A (Thermo) with 1% Omnipur agarose (EMD) in TAE (40 mM Tris-acetate, 1 mM EDTA, pH 8.3) at 7.4 V/cm for 20 min. Nanocrystals were diluted to 150 nM in TAE and mixed with 6× loading buffer (30% glycerol in H₂O) before loading onto the gel. Gels were visualized using handheld UV lamp and homemade gel imaging system.

ζ-Potential Measurement

ζ-Potential was measured on Malvern Zetasizer Nano ZS90 instrument. zeta-potentials were measured in 0.1× PBS, in a Dip Cell, with conductivities between 0.5-1 mS/cm·a nanocrystals coated with the betaine PILs (5 µM) were measured in 0.1×PBS buffer. Values are reported as the average of triplicate runs consisting of 100 scans each.

Dynamic Light Scattering (DLS)

Light-scattering analysis was performed using Malvern Zetasizer Nano ZS90 instrument. All nanocrystal samples were between 0.5 and 2 µM and filtered through a 0.02 µm filter before analysis. Typical count rates were between 85 and 150 kHz The resulting ACF was fitted using the DTS (Nano) software employing a non-negative least-squares fitting algorithm. Hydrodynamic radii were obtained from a mass-weighted size distribution analysis and reported as the mean of triplicate measurements.

Non-Specific Binding of Nanocrystals to Serum

The 570 nm emitting CdSe(CdZnS) nanocrystals (5 µL) of various surface coatings were mixed with 10% and 100% fetal bovine serum (95 µL) to a final concentration of ~0.5 µM. The mixture was incubated for 4 h at 37° C. with gentle mixing. The resultant nanocrystal size distribution was then measured using gel filtration chromatography. The mixture was injected into a Superose 6 GL10/300 column (GE Healthcare, Piscataway, N.J.) on an Agilient 1100 series HPLC with an in-line degasser, autosampler, diode array detector, and fluorescence detector (Roseville, Calif.). PBS (pH 7.4) was used as the mobile phase with a flow rate of 0.5 mL/min and an injection volume of 50 µL. In order to selectively measure the signal from the nanocrystal rather than FBS, the fluorescence detection at 570 nm with 250 nm excitation was chosen.

Transmission Electron Microscopy

The inorganic size of CdSe(CdS) nanocrystals was determined using a JEOL 200CX TEM operating at 200 kV. One drop of a dilute sample of nanocrystals in hexane precipitated two times using acetone was placed onto a Formvar coated copper grid, allowed to settle for 20 seconds, and wicked away using an absorbent tissue. Size analysis was performed on captured digital images using ImageJ 1.34s.

Intravital Microscopy

In vivo imaging was carried out using a custom-built multiphoton microscope (Olympus) with a Ti:Sapphire excitation laser at 840 nm (Mai-Tai HP, Spectra-Physics) and a 20×0.95 NA water-immersion lens (Olympus).

Mammary fat pad window chambers were implanted in female SCID mice as described previously. See, for example, Duda, D. G. et al. 2004; Vol. 64, p 5920-5924, which is incorporated by reference in its entirety. E0771 mammary tumors were implanted in the mammary fat pad in these chambers, and were allowed to grow for about two weeks until the tumors were roughly 4 mm in diameter and well-vascularized. All animal procedures were carried out following the Public Health Service Policy on Humane Care of Laboratory Animals and approved by the Institutional Animal Care and Use Committee of Massachusetts General Hospital.

To determine appropriate concentrations for equal photoluminescence intensity for green visible CdSe(CdS) and NIR InAs(ZnCdS) nanocrystals in solution, multiphoton imaging of mixed solutions of these nanocrystals in glass microslides (VitroCom) was conducted. See, for example, Brown, E. B. et al. Nat Med 2001, 7, 864-868, which is incorporated by reference in its entirety. A mixture at these concentrations was then prepared, and 150 µL of this solution was injected intravenously into the mouse via a bolus retro-orbital injection. From 15 minutes after injection, several adjacent fields of view near the periphery of the tumor were imaged. Imaging involved recording 3D stacks of roughly 150 um in depth. Imaging was continued for an hour, and the 3D stacks were processed using NIH ImageJ software.

Polyimidazole ligands incorporating sulfonate betaine or carboxylate betaine moieties can be used instead of conventional poly ethylene glycol moieties to provide water solubility. Without long repeating units of PEG, betaine PIL coated nanocrystals exhibited minimum increase of the hydrodynamic diameter after ligand exchange. Using the same size inorganic core/shell, betaine PIL coated nanocrystals were 4 nm smaller in hydrodynamic diameter than PEG PIL coated nanocrystals. In addition to the small size, strong hydration capacity of the polymers via electrostatic interaction of the betaine moieties results in low interaction with environments. Taking advantages of compact and biocompatible properties, we were able to image extravasation of nanocrystals from microvessels into tumors. Combining extraordinarily compact and biocompatible properties of betaine PILs with other general properties of PILs such as high QY, enhanced stability due to multidentate coordination of poly imidazole motif to nanocrystal surface and facile derivatizability, the betaine PILs can be widely used in biological studies well beyond the examples provided in the text.

What is claimed is:

1. A method of making a water-soluble semiconductor nanocrystal comprising:
    purifying imidazole monomers;
    purifying tertiary amine monomers;
    polymerizing imidazole and tertiary amine monomers to form a copolymer; and
    exchanging the ligand of a capped semiconductor nanocrystal with the imidazole polymer including a zwitterionic moiety,
    wherein the zwitterionic moiety includes betaine,
    wherein the copolymer on the each semiconductor nanocrystal increases a hydrodynamic diameter of the each semiconductor nanocrystal no more than 5 nm.

2. The method of claim 1, further comprising betainisation of the imidazole polymer before deprotecting a BOC group.

3. The method of claim 2, further comprising deprotecting the BOC group on the imidazole polymer before exchanging the ligand of a capped semiconductor nanocrystal.

4. The method of claim 1, wherein betainisation of the imidazole polymer results in a sulfonate betaine polymer.

5. The method of claim 1, wherein betainisation of the imidazole polymer results in a carboxylate betaine polymer.

6. The method of claim 1, wherein betainisation of the imidazole polymer results in a phosphocholine betaine polymer.

7. The method of biological in vivo imaging comprising:
introducing a copolymer including a betaine polyimidazole ligand including a zwitterionic moiety coated semiconductor nanocrystals to the subject wherein the copolymer on the each semiconductor nanocrystal increases a hydrodynamic diameter of the each semiconductor nanocrystal no more than 5 nm;
allowing the semiconductor nanocrystals to diffuse; and
visualizing the image with photon laser scanning microscopy.

8. The method of claim 7, wherein the photon laser scanning microscopy can be one-photon or two-photon.

9. The method of claim 7, wherein the semiconductor nanocrystals are used to image the extravasation of the nanocrystals from microvessels into a tumor.

10. A method of biological in vitro imaging comprising:
introducing a copolymer including a betaine polyimidazole ligand including a zwitterionic moiety coated semiconductor nanocrystals to a biological sample wherein the copolymer on the each semiconductor nanocrystal increases a hydrodynamic diameter of the each semiconductor nanocrystal no more than 5 nm;
allowing the semiconductor nanocrystals to diffuse;
collecting data from the semiconductor nanocrystals; and
visualizing an image from the data.

* * * * *